(12) United States Patent
Eidenschink et al.

(10) Patent No.: US 7,686,841 B2
(45) Date of Patent: *Mar. 30, 2010

(54) ROTATING BALLOON EXPANDABLE SHEATH BIFURCATION DELIVERY SYSTEM

(75) Inventors: Tracee Eidenschink, Wayzata, MN (US); Daniel Gregorich, Mound, MN (US); Karl A. Jagger, Deephaven, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/747,546

(22) Filed: Dec. 29, 2003

(65) Prior Publication Data

US 2005/0149161 A1 Jul. 7, 2005

(51) Int. Cl.
*A61F 2/06* (2006.01)
(52) U.S. Cl. ..................... 623/1.11
(58) Field of Classification Search ........... 606/108, 606/194, 200; 623/1.11, 1.12, 1.13, 1.23, 623/1.35; 604/96.01, 103.03–103.05, 171
See application file for complete search history.

(56) References Cited

U.S. PATENT DOCUMENTS

| | | | |
|---|---|---|---|
| 4,448,195 A | 5/1984 | Leveen et al. | 128/344 |
| 4,484,585 A | 11/1984 | Baier | 128/748 |
| 4,601,701 A | 7/1986 | Mueller, Jr. | 604/83 |
| 4,769,005 A | 9/1988 | Ginsburg et al. | 604/53 |
| 4,776,337 A | 10/1988 | Palmaz | 128/343 |
| 4,913,141 A | 4/1990 | Hillstead | 606/108 |
| 4,994,071 A | 2/1991 | MacGregor | 606/194 |
| 4,998,923 A | 3/1991 | Samson et al. | 606/194 |
| 5,019,085 A | 5/1991 | Hillstead | 606/108 |
| 5,120,308 A | 6/1992 | Hess | |
| 5,122,154 A | 6/1992 | Rhodes | 606/198 |
| 5,195,984 A | 3/1993 | Schatz | 606/195 |
| 5,219,335 A | 6/1993 | Willard et al. | |
| 5,219,355 A | 6/1993 | Parodi et al. | 606/191 |
| 5,246,421 A | 9/1993 | Saab | |
| 5,257,974 A | 11/1993 | Cox | |

(Continued)

FOREIGN PATENT DOCUMENTS

CA 2517380 9/2004

(Continued)

OTHER PUBLICATIONS

Foley et al. "Bifurcation Lesion Stenting", *The Thoraxcentre Journal*, vol. 8, No. 4, (1996)

(Continued)

*Primary Examiner*—Anhtuan T Nguyen
*Assistant Examiner*—Elizabeth Houston
(74) *Attorney, Agent, or Firm*—Crompton, Seager & Tufte, LLC

(57) ABSTRACT

A catheter assembly comprises a catheter, a rotatable sheath, a guidewire housing and a stent. The rotatable sheath is disposed about at least a portion of the catheter shaft and is rotatable thereabout. The stent is disposed about a stent receiving region of the rotatable sheath and at least a portion of the guidewire housing. The first end of the rotatable sheath extends beyond a proximal end region of the stent and the second end region of the rotatable sheath extends beyond a distal end region of the stent.

40 Claims, 20 Drawing Sheets

U.S. PATENT DOCUMENTS

| | | | |
|---|---|---|---|
| 5,316,023 A | 5/1994 | Palmaz et al. ............... 128/898 |
| 5,380,299 A * | 1/1995 | Fearnot et al. ............... 623/1.1 |
| 5,397,305 A | 3/1995 | Kawula et al. ............... 604/96 |
| 5,449,343 A | 9/1995 | Samson et al. |
| 5,449,382 A | 9/1995 | Dayton |
| 5,477,856 A | 12/1995 | Lundquist |
| 5,556,413 A | 9/1996 | Lam |
| 5,571,086 A | 11/1996 | Kaplan et al. ............... 604/96 |
| 5,609,627 A | 3/1997 | Goicoechea et al. ........... 623/1 |
| 5,632,763 A | 5/1997 | Glastra |
| 5,643,278 A | 7/1997 | Wijay |
| 5,670,161 A | 9/1997 | Healy et al. |
| 5,683,345 A | 11/1997 | Waksman et al. |
| 5,697,971 A | 12/1997 | Fischell et al. |
| 5,725,519 A | 3/1998 | Penner et al. |
| 5,735,859 A * | 4/1998 | Fischell et al. ............. 606/108 |
| 5,744,515 A | 4/1998 | Clapper |
| 5,749,825 A | 5/1998 | Fischell et al. |
| 5,755,734 A | 5/1998 | Richter et al. |
| 5,755,735 A | 5/1998 | Richter et al. |
| 5,755,778 A | 5/1998 | Kleshinski |
| 5,772,669 A | 6/1998 | Vrba |
| 5,776,141 A * | 7/1998 | Klein et al. ................ 623/1.11 |
| 5,797,952 A | 8/1998 | Klein |
| 5,807,398 A * | 9/1998 | Shaknovich ............... 623/1.11 |
| 5,817,100 A | 10/1998 | Igaki |
| 5,824,055 A | 10/1998 | Spiridigliozzi et al. ......... 623/1 |
| 5,836,952 A | 11/1998 | Davis et al. |
| 5,843,027 A | 12/1998 | Stone et al. |
| 5,873,906 A | 2/1999 | Lau et al. |
| 5,876,374 A | 3/1999 | Alba et al. |
| 5,893,868 A | 4/1999 | Hanson et al. |
| 5,906,640 A | 5/1999 | Penn et al. |
| 5,908,405 A | 6/1999 | Imran et al. |
| 5,921,995 A | 7/1999 | Kleshinski |
| 5,935,161 A | 8/1999 | Robinson et al. |
| 5,941,908 A | 8/1999 | Goldsteen et al. |
| 5,951,569 A | 9/1999 | Tuckey et al. |
| 5,957,929 A | 9/1999 | Brenneman |
| 5,961,546 A | 10/1999 | Robinson et al. |
| 5,961,548 A | 10/1999 | Shmulewitz |
| 6,013,092 A | 1/2000 | Dehdashtian et al. |
| 6,015,424 A * | 1/2000 | Rosenbluth et al. ......... 606/194 |
| 6,017,362 A | 1/2000 | Lau ................ 623/1 |
| 6,027,460 A | 2/2000 | Shturman ................ 600/585 |
| 6,033,434 A | 3/2000 | Borghi ............... 623/1 |
| 6,048,350 A | 4/2000 | Vrba |
| 6,048,361 A | 4/2000 | Von Oepen ............... 623/1 |
| 6,056,722 A | 5/2000 | Jayaraman ............... 604/102 |
| 6,056,775 A | 5/2000 | Borghi et al. ............... 623/1.16 |
| 6,059,813 A | 5/2000 | Vrba et al. ............... 606/198 |
| 6,071,286 A | 6/2000 | Mawad ............... 606/108 |
| 6,077,297 A | 6/2000 | Robinson et al. ........... 623/1.11 |
| 6,090,127 A | 7/2000 | Globerman ............... 606/194 |
| 6,096,073 A | 8/2000 | Webster et al. ............... 623/1.16 |
| 6,099,497 A | 8/2000 | Adams et al. ............... 604/96.01 |
| 6,110,191 A | 8/2000 | Dehdashtian et al. ........ 606/192 |
| 6,117,156 A | 9/2000 | Richter et al. ............... 606/194 |
| 6,120,522 A | 9/2000 | Vrba et al. ............... 606/190 |
| 6,132,450 A | 10/2000 | Hanson et al. ............... 606/198 |
| 6,143,014 A | 11/2000 | Dehdashtian et al. ........ 606/192 |
| 6,143,016 A * | 11/2000 | Bleam et al. ............... 606/194 |
| 6,146,415 A | 11/2000 | Fitz ............... 623/1.11 |
| 6,152,944 A | 11/2000 | Holman et al. ............... 623/1.11 |
| 6,165,195 A | 12/2000 | Wilson et al. ............... 606/194 |
| 6,165,196 A | 12/2000 | Stack et al. |
| 6,165,210 A | 12/2000 | Lau et al. ............... 623/1.12 |
| 6,187,015 B1 | 2/2001 | Brenneman ............... 606/108 |
| 6,190,360 B1 | 2/2001 | Iancea et al. ............... 604/164.09 |
| 6,190,393 B1 | 2/2001 | Bevier et al. ............... 606/108 |
| 6,210,380 B1 | 4/2001 | Mauch ............... 604/284 |
| 6,210,431 B1 | 4/2001 | Power ............... 623/1.11 |
| 6,221,090 B1 | 4/2001 | Wilson ............... 606/194 |
| 6,221,097 B1 | 4/2001 | Wang et al. ............... 623/1.11 |
| 6,224,587 B1 | 5/2001 | Gibson ............... 604/528 |
| 6,238,410 B1 | 5/2001 | Vrba et al. ............... 606/198 |
| 6,246,914 B1 | 6/2001 | De la Rama et al. ........ 607/122 |
| 6,254,593 B1 | 7/2001 | Wilson ............... 606/1.11 |
| 6,258,052 B1 | 7/2001 | Milo ............... 604/22 |
| 6,258,073 B1 | 7/2001 | Mauch ............... 604/284 |
| 6,264,688 B1 | 7/2001 | Herklotz et al. ............... 623/1.16 |
| 6,280,466 B1 | 8/2001 | Kugler et al. ............... 623/1.12 |
| 6,287,277 B1 | 9/2001 | Yan ............... 604/96.01 |
| 6,287,330 B1 | 9/2001 | Johansson et al. ............ 623/1.13 |
| 6,290,673 B1 | 9/2001 | Shanley ............... 604/102.02 |
| 6,299,636 B1 | 10/2001 | Schmitt et al. ............... 623/1.2 |
| 6,302,906 B1 | 10/2001 | Goicoechea et al. ......... 623/1.11 |
| 6,319,275 B1 | 11/2001 | Lashinski et al. ........... 623/1.11 |
| 6,322,548 B1 | 11/2001 | Payne et al. ............... 604/500 |
| 6,350,278 B1 | 2/2002 | Lenker et al. |
| 6,361,544 B1 | 3/2002 | Wilson et al. ............... 606/194 |
| 6,361,555 B1 | 3/2002 | Wilson ............... 623/1.11 |
| 6,364,893 B1 | 4/2002 | Sahatjian et al. ............. 606/194 |
| 6,371,978 B1 | 4/2002 | Wilson ............... 623/1.11 |
| 6,375,660 B1 | 4/2002 | Fischell et al. ............... 606/108 |
| 6,379,372 B1 | 4/2002 | Dehdashtian et al. ........ 606/192 |
| 6,387,120 B2 | 5/2002 | Wilson et al. ............... 623/1.11 |
| 6,391,050 B1 | 5/2002 | Broome ............... 623/1.11 |
| 6,406,487 B2 | 6/2002 | Brenneman ............... 623/1.11 |
| 6,406,489 B1 | 6/2002 | Richter et al. ............... 623/1.16 |
| 6,416,529 B1 | 7/2002 | Holman et al. ............... 606/194 |
| 6,436,104 B2 | 8/2002 | Hojeibane ............... 606/108 |
| 6,443,980 B1 | 9/2002 | Wang et al. ............... 623/1.35 |
| 6,471,672 B1 | 10/2002 | Brown et al. |
| 6,475,166 B1 | 11/2002 | Escano ............... 600/585 |
| 6,482,211 B1 | 11/2002 | Choi ............... 606/108 |
| 6,488,694 B1 | 12/2002 | Lau et al. ............... 606/194 |
| 6,508,835 B1 | 1/2003 | Shaolian et al. ............... 623/1.35 |
| 6,514,281 B1 | 2/2003 | Blaeser et al. ............... 623/1.12 |
| 6,520,983 B1 | 2/2003 | Colgan et al. ............... 623/1.11 |
| 6,520,988 B1 | 2/2003 | Colombo et al. ............ 623/1.35 |
| 6,530,947 B1 | 3/2003 | Euteneuer et al. ........... 623/1.11 |
| 6,533,805 B1 | 3/2003 | Jervis ............... 623/1.11 |
| 6,540,719 B2 | 4/2003 | Bigus et al. ............... 604/96.01 |
| 6,554,841 B1 | 4/2003 | Yang ............... 606/108 |
| 6,569,180 B1 * | 5/2003 | Sirhan et al. ............... 606/194 |
| 6,582,459 B1 | 6/2003 | Lau et al. ............... 623/1.11 |
| 6,589,262 B1 | 7/2003 | Honebrink et al. ........... 606/191 |
| 6,596,020 B2 * | 7/2003 | Vardi et al. ............... 606/108 |
| 6,599,315 B2 | 7/2003 | Wilson ............... 623/1.11 |
| 6,602,226 B1 | 8/2003 | Smith et al. ............... 604/103.05 |
| 6,607,506 B2 | 8/2003 | Kletschka ............... 604/96.01 |
| 6,613,067 B1 | 9/2003 | Johnson ............... 606/194 |
| 6,629,981 B2 | 10/2003 | Bui et al. ............... 606/108 |
| 6,629,992 B2 | 10/2003 | Bigus et al. |
| 6,660,030 B2 | 12/2003 | Shaolian et al. ............. 623/1.11 |
| 6,669,718 B2 | 12/2003 | Besselink ............... 623/1.11 |
| 6,692,483 B2 | 2/2004 | Vardi et al. ............... 604/529 |
| 6,695,863 B1 * | 2/2004 | Ramzipoor et al. ......... 606/194 |
| 6,872,215 B2 | 3/2005 | Crocker et al. |
| 7,070,613 B2 | 7/2006 | Weber et al. |
| 7,147,655 B2 * | 12/2006 | Chermoni ............... 623/1.11 |
| 7,238,197 B2 | 7/2007 | Sequin et al. |
| 2001/0049548 A1 * | 12/2001 | Vardi et al. ............... 623/1.11 |
| 2002/0019664 A1 | 2/2002 | Douglas ............... 623/1.35 |
| 2002/0019665 A1 | 2/2002 | Dehdashtian et al. ....... 623/1.35 |
| 2002/0022874 A1 | 2/2002 | Wilson ............... 623/1.11 |
| 2002/0038140 A1 | 3/2002 | Yang et al. ............... 623/1.12 |
| 2002/0038141 A1 | 3/2002 | Yang et al. ............... 623/1.12 |
| 2002/0072755 A1 * | 6/2002 | Bigus et al. ............... 606/108 |
| 2002/0111675 A1 | 8/2002 | Wilson ............... 623/1.35 |
| 2002/0116045 A1 | 8/2002 | Eidenschink ............... 623/1.11 |
| 2002/0120320 A1 | 8/2002 | Wang et al. ............... 623/1.11 |
| 2002/0165598 A1 * | 11/2002 | Wahr et al. ............... 623/1.11 |

| | | | |
|---|---|---|---|
| 2003/0023298 A1 | 1/2003 | Jervis | 623/1.11 |
| 2003/0055483 A1 | 3/2003 | Gumm | 623/1.11 |
| 2003/0055484 A1 | 3/2003 | Lau et al. | 623/1.13 |
| 2003/0130716 A1 | 7/2003 | Weber et al. | 623/1.11 |
| 2003/0181923 A1 | 9/2003 | Vardi | 606/108 |
| 2003/0195546 A1* | 10/2003 | Solar et al. | 606/192 |
| 2004/0172121 A1 | 9/2004 | Eidenschink et al. | 623/1.11 |
| 2008/0119923 A1 | 5/2008 | Tran et al. | |

FOREIGN PATENT DOCUMENTS

| | | |
|---|---|---|
| CA | 2533306 | 3/2005 |
| CA | 2556693 | 9/2005 |
| CA | 2569567 | 12/2005 |
| DE | 297 01 758 | 5/1997 |
| EP | 1601312 | 9/2007 |
| FR | 2 678 508 A1 | 1/1993 |
| WO | 0044307 | 8/2000 |
| WO | 03/017872 A1 | 3/2003 |
| WO | 03/055414 A1 | 7/2003 |
| WO | 03/061529 | 7/2003 |
| WO | 2004/075792 A1 | 9/2004 |
| WO | 2005025458 | 3/2005 |
| WO | 2005067818 | 7/2005 |
| WO | 2005070334 | 8/2005 |
| WO | 2005079902 | 9/2005 |
| WO | 2005122958 | 12/2005 |

OTHER PUBLICATIONS

Schampaert, MD, Erick et al., "The V-Stent: A Novel Technique for Coronary Bifurcation Stenting", *Catheterization and Cardiovascular Diagnosis*, 39:320-326 (1996).

Pomerantz, MD, et al., "Distortion of Palmaz-Schatz Stent Geometry Following Side-Branch Balloon Dilation Through the Stent in a Rabbit Model", *Catheterization and Cardiovascular Diagnosis*, 40:422-426 (1997).

Palmaz, MD, et al., "Aortic Bifurcation Stenosis: Treatment with Intravascular Stents", *Journal of Vascular and Interventional Radiology*, vol. 2, No. 3, pp. 319-323 (Aug. 1991).

Oda, MD., et al., "Fork Stenting for Bifurcational Lesion", Journal of Interventional Cardiology, vol. 9, No. 6, pp. 445-454 (Dec. 1996).

Nakamura et al., "Techniques for Palmaz-Schatz Stent Deployment in Lesions With a Large Side Branch", Catheterization and Cardiovascular Diagnosis, vol. 34, pp. 353-361 (1995).

U.S. Appl. No. 10/375,689 filed, Feb. 27, 2003, Eidenschink.
U.S. Appl. No. 10/747,546 filed, Dec. 29, 2003, Eidenschink et al.
U.S. Appl. No. 10/657,472 filed, Sep. 8, 2003, Eidenschink, et al.
U.S. Appl. No. 10/757,646 filed, Jan. 13, 2004, Eidenschink, et al.
U.S. Appl. No. 10/780,937 filed, Feb. 18, 2004, Eidenschink, et al.
U.S. Appl. No. 10/784,337 filed, Feb. 23, 2004, Eidenschink, et al.
U.S. Appl. No. 10/863,724 filed, Jun. 8, 2004, Eidenschink, et al.
"Medical Urethanes Overview," Noveon, the Specialty Chemicals Innovator, 11 pages, prior to Jan. 13, 2004.

* cited by examiner

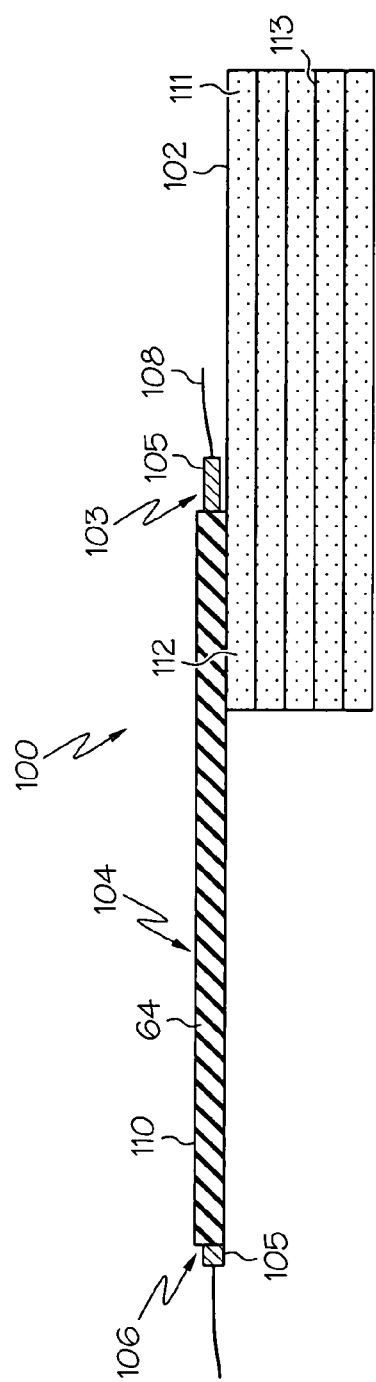
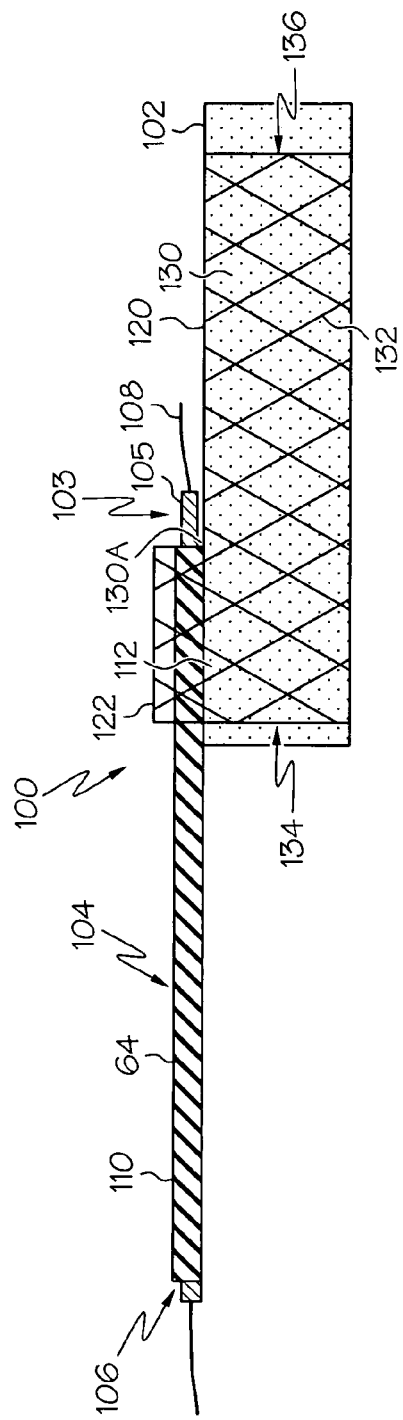
FIG. 1
FIG. 2

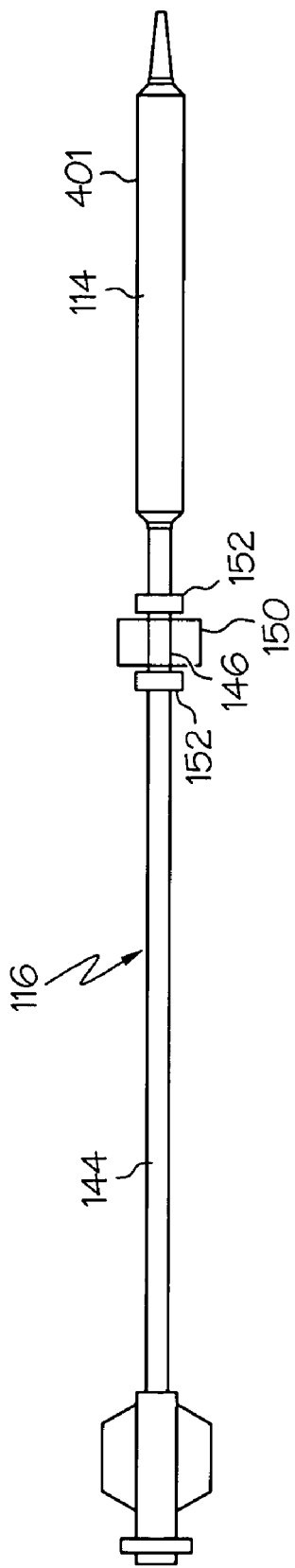
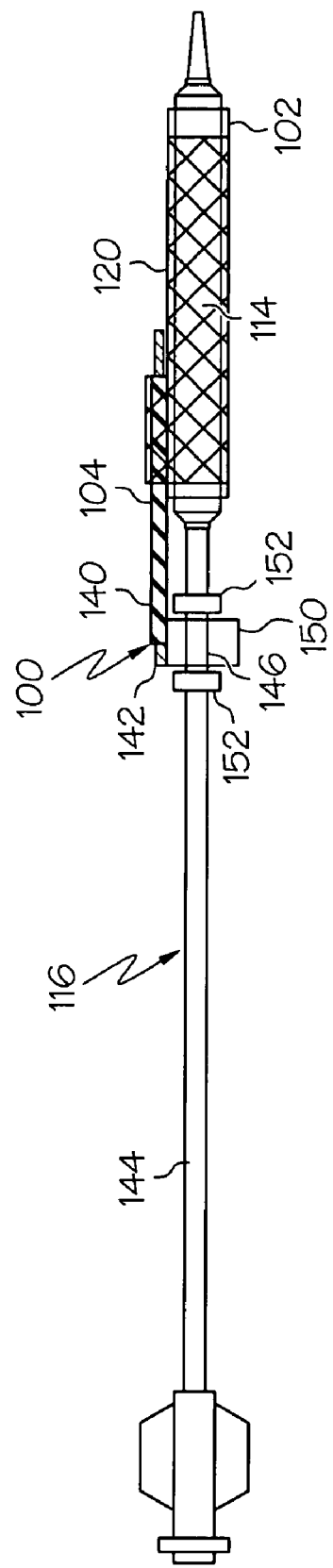
FIG. 3
FIG. 4

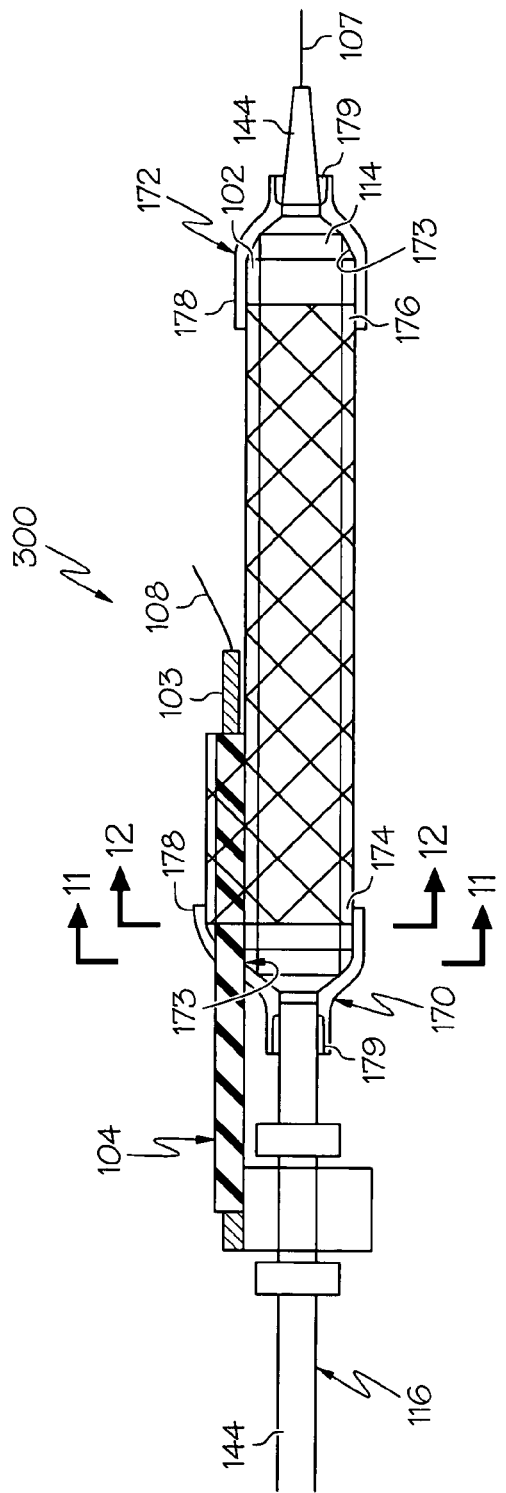
FIG. 10
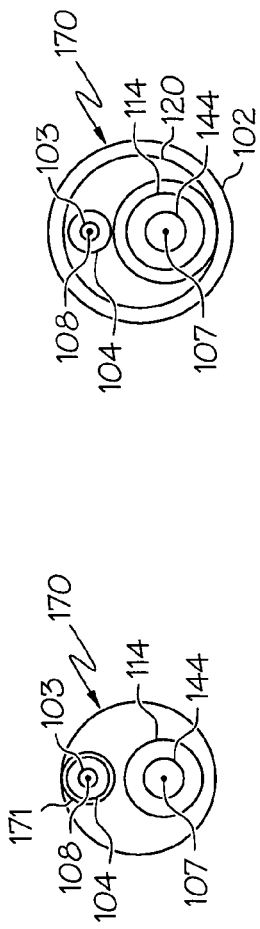
FIG. 11
FIG. 12

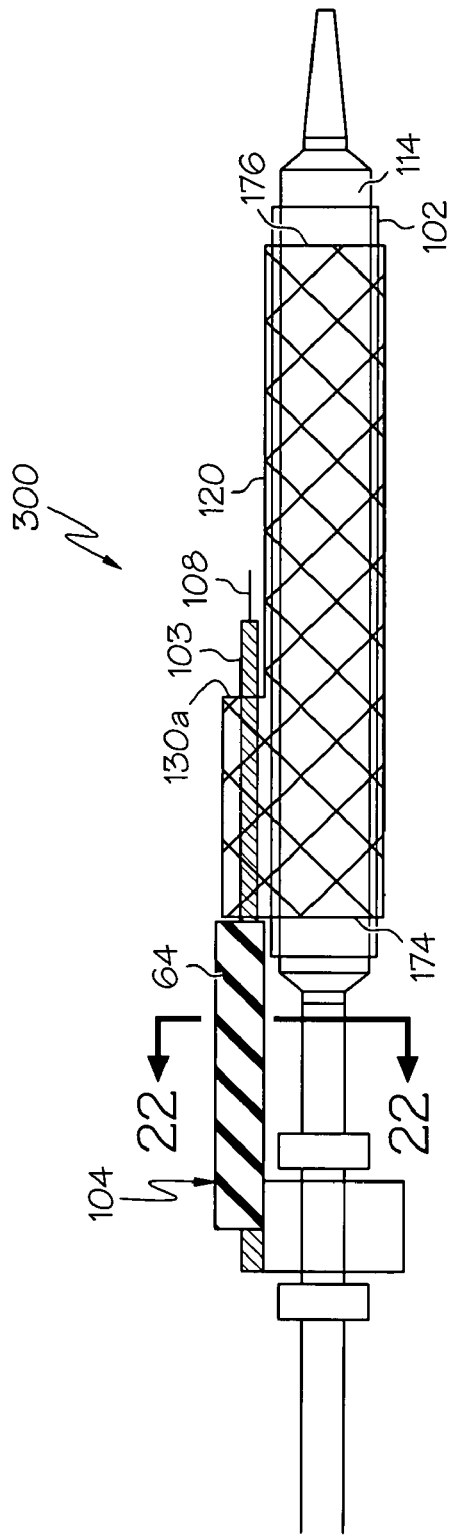
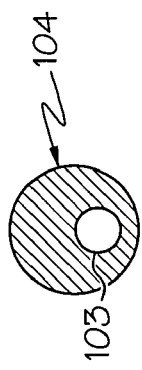
FIG. 21
FIG. 22

ROTATING BALLOON EXPANDABLE SHEATH BIFURCATION DELIVERY SYSTEM

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Description of the Related Art

Catheter systems such as angioplasty catheters, and stent delivery systems, as well as the stents associated therewith, are widely used in the treatment of stenoses, aneurysms, lesions, and other abnormalities within blood vessels and other body lumens. Intravascular stents are used in coronary, renal, and carotid arteries, for example, to maintain an open passage through the artery. In patients whose coronary heart disease consists of focal lesions, stents have proven effective. For example, where only a single coronary artery is clogged or where there are short blockages in more than a single artery, stents have been used with a great amount of success. An intravascular stent may be positioned in a clogged artery by a catheter and is often set in place by inflating a balloon upon which the stent is mounted. This expands the diameter of the stent and opens the previously clogged artery. The balloon is then deflated and removed from the patient while the stent retains an open passage through the artery.

Treatment at bifurcation sites has been difficult. Although efforts have been made to use a stent at bifurcations, these sites have previously been problematic to treat. The specialty stents designed for bifurcations generally need specific alignment, radially as well as longitudinally. For example, U.S. Pat. No. 5,749,825 is representative of a catheter system that is intended to treat stenoses at an arterial bifurcation. The disclosure of U.S. Pat. No. 5,749,825 is hereby incorporated by reference.

A stent delivery system employing a stent assembly with branches intended for deployment in the adjacent branches of a vessel bifurcation has been proposed to allow placement of a portion of the assembly in both a primary passage, such as an artery, and a secondary passage, such as a side branch artery. Additionally, these stents generally have an opening which allows for unimpeded blood flow into the side branch artery. However, problems are still encountered in orienting the stent relative to the side branch at the bifurcation of the primary and secondary passages. Moreover, such bifurcated assemblies are typically specially manufactured at an increased cost over a more standard stent intended for single vessel deployment.

In delivering a stent to a vessel location, many current devices rely on either passive torque (e.g., pushing the stent forward and allowing the stent that is fixed on the guidewire/balloon to passively rotate itself into place) or creating torque from outside of the patient to properly orient the medical device in the passage. These devices and methods of achieving proper angular orientation have not been shown to be effective in properly placing and positioning the stent. In addition, many catheter systems which are currently utilized to deploy a stent or other implantable device into a body lumen do not provide adequate stent edge protection prior to delivery.

Thus, a need exists to provide a catheter which is capable of allowing a medical device such as a stent to be easily maneuvered and aligned at a vessel bifurcation or other location, while also adequately protecting the edges of the stent during advancement of the catheter through the tortuous confines of a body lumen.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

Some embodiments of the present invention include a freely rotating deployment assembly for a stent assembly for maintaining side branch access and protection.

At least one embodiment of the invention includes a medical device with a balloon catheter shaft and a rotating sheath such as is described in U.S. patent application Ser. No. 10/375,689, filed Feb. 27, 2003 and U.S. patent application Ser. No. 10/657,472, filed Sep. 8, 2003 both of which are entitled Rotating Balloon Expandable Sheath Bifurcation Delivery, the entire content of both being incorporated herein by reference, wherein the ends of the sheath and/or stent are provided with one or more protective elements.

In at least one embodiment the sheath has one or more end regions and an intermediate region, wherein the intermediate region has an outer diameter less than that of either or both end regions. In some embodiments the intermediate region defines a stent mounting region wherein the stent is disposed prior to delivery between end regions of the sheath.

In some embodiments prior to expansion one or both cones of the balloon have a diameter that is greater than the unexpanded or predeployed diameter of the sheath and/or stent disposed thereon.

In at least one embodiment the catheter further comprises one or more end sleeves or socks, wherein each sleeve has a first end engaged to the catheter shaft adjacent to an end of the balloon. In some embodiments the first end of each sleeve is freely rotatable about the catheter shaft. In at least one embodiment, a sleeve has a second end, which prior to deployment of the stent, is disposed about an end of the stent and during deployment of the stent is retracted therefrom to release the stent into a body lumen.

In some embodiments prior to deployment of the stent a proximal sleeve is engaged to the proximal end of the stent and a distal sleeve is engaged to a distal end of the stent. In some embodiments a single sleeve is engaged to only one end of the stent prior to deployment.

In some embodiments the medical device comprises a secondary guidewire lumen housing, which itself comprises a reinforcing member, such as a polymer tube of PEBAX, peek, polyimide, etc., a braided tube of metal wire or other material, a hypotube, or other device engaged to the sheath and engaged to the collar. In some embodiments an inner member is positioned within the reinforcing member to define the secondary guidewire lumen. In some embodiments the material of the inner member is more flexible than the material of the reinforcing member. In some embodiments the inner member is longer than the reinforcing member and at least one end of the inner member extends beyond at least one end of the reinforcing member.

In at least one embodiment the inner member is concentrically disposed within the reinforcing member. In some embodiments the inner member is asymmetrically disposed within the reinforcing member.

In at least one embodiment the proximal end of the reinforcing member is proximally adjacent to the stent. In some embodiments the proximal end of the reinforcing member is tapered. In at least one embodiment the reinforcing member is positioned such that at least a portion of the reinforcing member is radially offset from the distal end of the stent.

In at least one embodiment the rotatable sheath has a length longer than the stent. In some embodiments one or both ends of the sheath are folded back over the corresponding ends of the stent prior to delivery. When the stent is deployed the one or both ends of the sheath slidingly retract off of the stent, thereby freeing the ends of the stent for deployment. In some embodiments only the distal end of the sheath is folded over the distal end of the stent prior to delivery. In at least one embodiment the proximal end of the sheath defines a proximal slit or is tapered to accommodate the position of the secondary guidewire lumen housing, such that the proximal end of the sheath may be folded over at least a portion of the proximal end of the stent prior to delivery.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

FIG. 1 is a side view of an embodiment of the invention, comprising a rotating sheath assembly.

FIG. 2 is a side view of the embodiment shown in FIG. 1 shown configured for delivery of a stent.

FIG. 3 is a side view of an embodiment of the invention comprising a catheter assembly. The catheter assembly is provided with a rotating collar.

FIG. 4 is a side view of the catheter assembly of FIG. 3 and further comprising the rotating sheath assembly and stent of FIG. 2.

FIG. 10 is a side view of an embodiment of the embodiment of the invention shown in FIG. 4 which includes protective sleeves.

FIG. 11 is a cross-sectional view of a portion of the system shown in FIG. 10 corresponding to section A.

FIG. 12 is a cross-sectional view of a portion of the system shown in FIG. 10 corresponding to section B.

FIG. 21 is a side view of an embodiment of the invention wherein the secondary guidewire housing is radially offset from the proximal end of the stent.

FIG. 22 is a cross-sectional view of a portion of the system shown in FIG. 21 corresponding to section C.

DETAILED DESCRIPTION OF THE INVENTION

Figure 5:
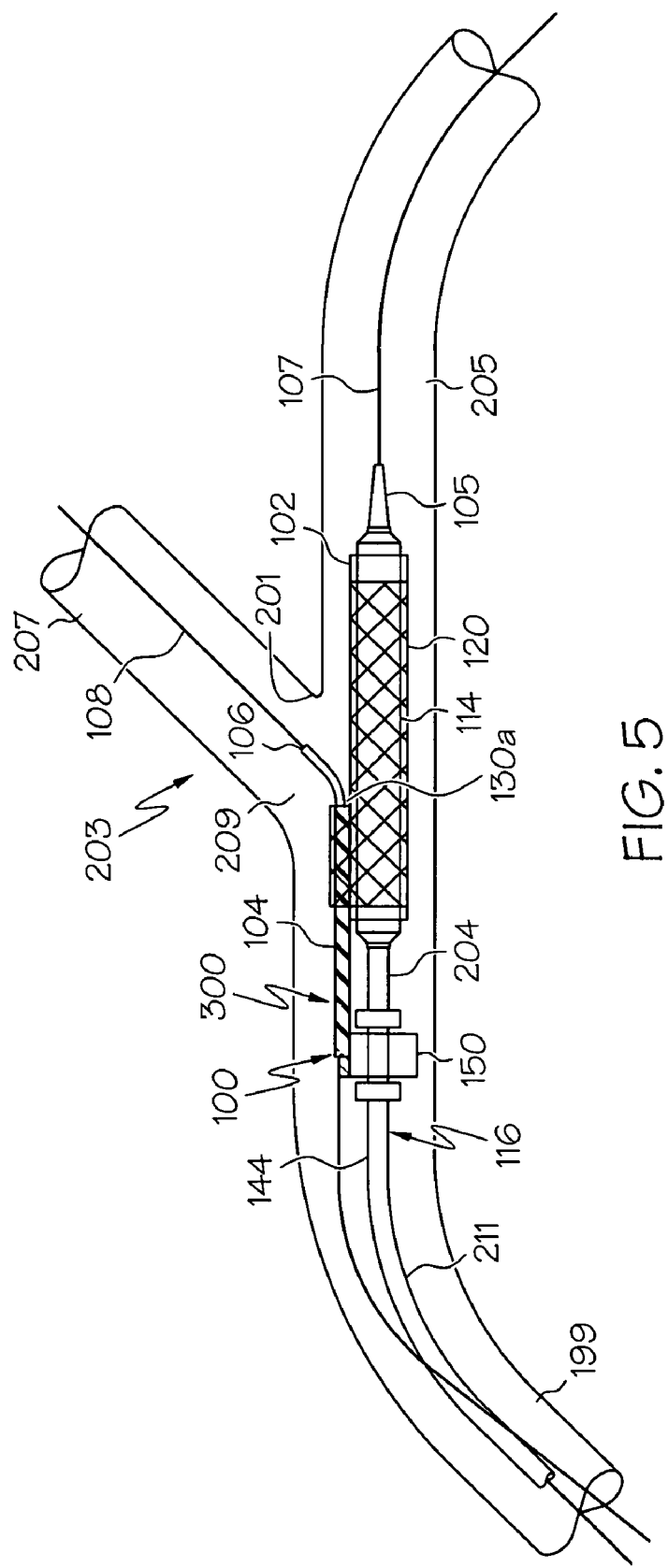
FIG. 5 is a side view of an embodiment of the invention wherein the catheter assembly of FIG. 4 is shown being advanced along a guidewire to a vessel bifurcation prior to delivery of the stent.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Referring now to the drawings which are for the purposes of illustrating embodiments of the invention only and not for purposes of limiting same, in at least one embodiment of the invention, an example of which is shown in FIG. 1 a rotating sheath assembly 100 is shown which comprises a tubular sleeve or sheath 102 and a positioning or secondary guidewire housing 104. The housing 104 defines a secondary guidewire lumen 106 through which a secondary guidewire 108 may be passed.

Though the housing 104 may be constructed of a wide variety of materials including metal plastic, etc., in at least one embodiment the housing 104 is an external reinforcing member or hypotube 64.

The hypotube 64 may comprise stainless steel, one or more polymer materials or other material. In some embodiments the housing 104 is provided with one or more openings 110 along its length. In at least one embodiment the housing 104 is spiral cut to provide at least a continuous opening 110 which acts to provide improve the flexibility of the housing 104.

In at least one embodiment the secondary guidewire housing 104 further comprises an inner shaft 103, about which the hypotube 64 is disposed. Alternatively, the inner shaft 103 and hypotube 64 may be of a single piece construction wherein the housing 104 is formed using a 'bumped' extrusion and then scored for improved flexibility. In at least one embodiment the inner shaft 103 is a flexible hollow tubular member which extends distally beyond the distal end of the hypotube 64. In some embodiments both the hypotube 64 and the inner shaft 103 are scored, cut or otherwise provided with improved flexibility over a more rigid continuous shaft. In some embodiments flexibility of the housing 104 may be improved by manufacturing the housing 104, or a portion thereof, to include segmented rings; a pattern of cuts, indentations, etc; and or a corrugated construction.

This distal and/or proximal tips 105 of the inner shaft 103 provides the housing with a flexible protective sheath about the guidewire 108 as it passes out of the secondary guidewire lumen 106. Such a protective covering may prevent the guidewire 108 from excessively rubbing against the wall 201 of the vessel 199, such as in the manner depicted in FIG. 5; even where the secondary guidewire 108 exits the secondary lumen 106 at a significant angle. The inner shaft 103 may be constructed of any of a variety of flexible materials such as: high density polyurethane (HDPE), PEBAX, nylon, urethane, and/or other materials in a single layer, multi-layer and/or braided configuration.

In some embodiments the shaft 144 of the catheter 116 defines a primary guidewire housing 211 through which a primary guidewire 107 may be advanced. In use guidewires 107 and 108 are passed through a lumen or other body vessel 209 to a bifurcation 203. Primary guidewire 107 is then advanced into a primary branch of passage 205 of the bifurcation 203 while the secondary guidewire 108 is advanced into the adjacent or secondary branch 207 of the bifurcation 203. As the system is advanced along both guidewires 107 and 108, as a result of the divergent paths defined by the guidewires 107 and 108, the rotatable sleeve 104 will rotate the stent 120 into a desired position so that the secondary opening 130a of the stent is aligned with the secondary passage 207. In at least one embodiment, the system 300 is a fixed wire system, and as such the use of the primary guidewire is unnecessary. In some embodiments the catheter 116 is an over-the-wire, MONORAIL®, or other type of catheter 116 which requires the primary guidewire 107.

In some embodiments at least a distal portion of the housing 104 is engaged to at least a proximal portion of the sheath 102 at an engagement site 112. The manner or mechanism of engagement between the sheath and housing 104 may be by bonding, welding, adhering adhesively engaging, mechanically engaging or otherwise connecting the surfaces of the respective sheath 102 and housing 104.

The sheath 102 is a hollow tube of sheath material that is configured to be placed over the balloon 114 or other region of a catheter 116, such as in the manner illustrated in FIGS. 3 and 4. The sheath 102 is further configured to be rotatable about the catheter shaft and/or balloon 114, even when a stent 120 has been positioned about and/or affixed to the sheath 102.

In order to ensure that the sheath 102 is rotatable about a balloon 114, even with a stent 120 crimped on to the sheath 102 and the catheter is being advanced through the a body, the sheath 102 may be constructed of a variety of low friction materials such as PTFE, HDPE, etc. In at least one embodiment the sheath 102 is at least partially constructed of a hydrophilic material, such as hydrophilic polymers such as; TECOPHILIC® material available from Thermedics Polymer Products, a division of VIASYS Healthcare of Wilmington, Mass.; TECOTHANE®, also available from Thermedics Polymer Products; hydrophilic polyurethanes, and/or aliphatic, polyether-based thermoplastic hydrophilic polyurethane; and any other material that provides the sheath 102 with the ability to rotate freely about the balloon 114 when in the "wet" state, such as when the catheter is exposed to body fluids during advancement through a vessel. Suitable sheath materials may also provide the sheath with rotatability in the "dry", or pre-insertion, state, but with the application of a greater amount of force than when in the wet state, such materials are referred to herein as being tecophilic.

A sheath 102 at least partially constructed from tecophilic material provides the sheath 102 with the ability to rotate freely about the balloon 114 when in the "wet" state, such as when the catheter is exposed to body fluids during advancement through a vessel. The tecophilic sheath 102 is also capable of rotation in the "dry", or pre-insertion, state, but with the application of a greater amount of force than when in the wet state.

In some embodiments the sheath 102 may be constructed of one or multiple materials, in one or more layers. For example, the sheath 102 may comprise an outer layer of a softer material than that of the material used in constructing an inner layer, such as has been previously described. In some embodiments, an example of which is shown in FIG. 1, the sheath 102 may be comprised of a matrix of a first material 111 and have one or more supportive stripes, strands, members or areas of a second supportive material 113 within, external to or internal to such a matrix.

The composition of the sheath 102 material, whether a single, multiple layer or stripe reinforced extrusion may include essentially any appropriate polymer or other suitable materials. Some example of suitable polymers include Hydrophilic Polyurethanes, Aromatic Polyurethanes, Polycarbonate base Aliphatic Polyurethanes, Engineering polyurethane, Elastomeric polyamides, block polyamide/ethers, polyether block amide (PEBA, for example available under the trade name PEBAX), and Silicones, Polyetherester (for example a polyether-ester elastomer such as Arnitel available from DSM Engineering Plastics), Polyester (for example a polyester elastomer such as Hytrel available from Du Pont), or linear low density polyethylene (for example Rexell).

Example of suitable re-inforcing materials whether alone or blended with other materials, mixtures or combination or copolymers include all Polyamides (for example, Durethan available from Bayer or Cristamid available from ELF Atochem), polyethylene (PE). Marlex high-density polyethylene, polyetheretherketone (PEEK), polyimide (PI), and polyetherimide (PEI), liquid crystal polymers (LCP), and Acetal (Delrin or Celcon).

In some embodiments the inner surface of the sheath 102 or the outer surface of the balloon 114 may include a coating of one or more low friction materials or include one or more low friction materials in its construction. Such a coating 401 is shown in FIG. 3, as being depicted on the surface of the balloon 114 before assembly 100 has been placed thereabout, such as is depicted in FIG. 4. Coating 401 may however by placed between the balloon 114 and sheath 102 at any time. Some examples of a suitable coating material include but are not limited to: hydrogel, silicon, and/or BIOSLIDE® available from SciMed Life Systems, Inc. of Maple Grove Minn.

As mentioned above, the sheath 102 is configured to be freely rotatable about a balloon of a catheter even when a stent 120, such as is shown in FIGS. 2 and 4 is crimped onto the sheath 102. When properly positioned on the sheath 102, a proximal portion 122 of the stent 120 is also disposed about at least a portion of the secondary guidewire housing 104. When properly positioned about the sheath 102 and the housing 104, at least a portion of the housing 104 and/or the secondary guidewire 108 extends distally through a cell opening 130 of the stent 120.

Figure 6:
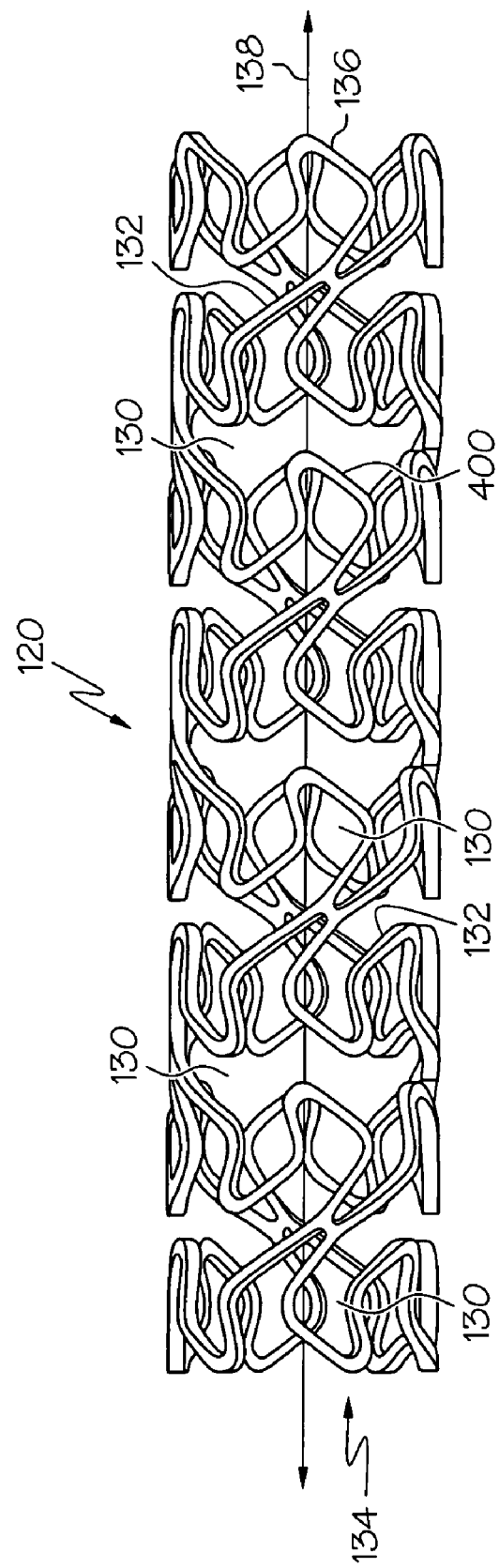
FIG. 6 is a side perspective view of an embodiment of the invention comprising a stent, such as that shown in FIG. 2.

Stent 120 may be a stent, such as is shown in FIG. 6, which is at least partially constructed of a plurality of interconnected struts, connectors or members 132. The stent 132 defines a proximal opening 134, a distal opening 136 and a flow path 138 therebetween. The cell openings 130 are in fluid communication with the flow path 138.

When the secondary guidewire 108 and/or the secondary guidewire housing 104 is threaded through one of the cell openings 130 when the stent is positioned onto the assembly 100, such as is shown in FIGS. 2 and 4, the members 132 that define the selected cell opening 130a, as well as the shape of the opening 130a through which the secondary guidewire 108 exits the stent, may be distorted or modified in order to accommodate the passage of secondary guidewire 108 and/or the secondary guidewire housing 104 therethrough.

Figure 7:
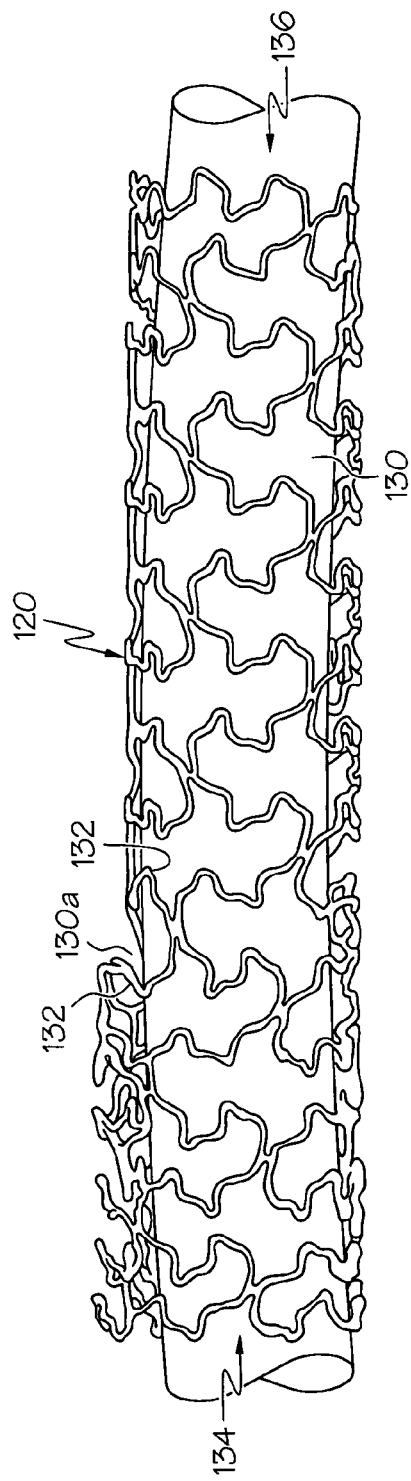
FIG. 7 is a side perspective view of the stent shown in FIG. 6 wherein a side branch opening is shown formed from the enlargement of a cell opening in the stent wall.
Figure 8:
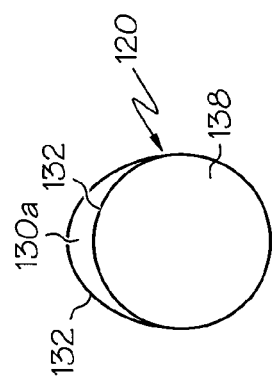
FIG. 8 is a cross-sectional view of the stent of FIG. 7.

The modified cell opening 130a, hereinafter referred to as secondary opening 130a, is positioned on the stent 120 between the proximal opening 134 and the distal opening 136 and is depicted in FIGS. 7 and 8. It is noted that any type of stent may be provided with secondary opening 130a and that the present invention is not limited to only the particular type of stent design, configuration or structure shown.

It should be noted that when the stent 120 is placed on the assembly in the manner described above, the distortion of the secondary opening 130a and the adjacent members 132 is of a minimal extent, and is provide only to allow sliding passage of the secondary guidewire 108, and if desired a distal portion of the secondary guidewire housing 104, through the secondary opening 130a. As such, the actual size of the secondary opening 130a may be substantially similar, or only marginally different than that of the surrounding cell openings 130.

It should also be further noted that while stent 120 may be a standard "single vessel" stent that is provided with a secondary opening 130a in the manner described above, the stent 120 may also be a bifurcated stent having a trunk or stem portion, with one or more leg portions and/or branch openings adjacent thereto, through one of which the secondary guidewire may be passed. Such bifurcated stents and stent assemblies are well known in the art.

Figure 9:
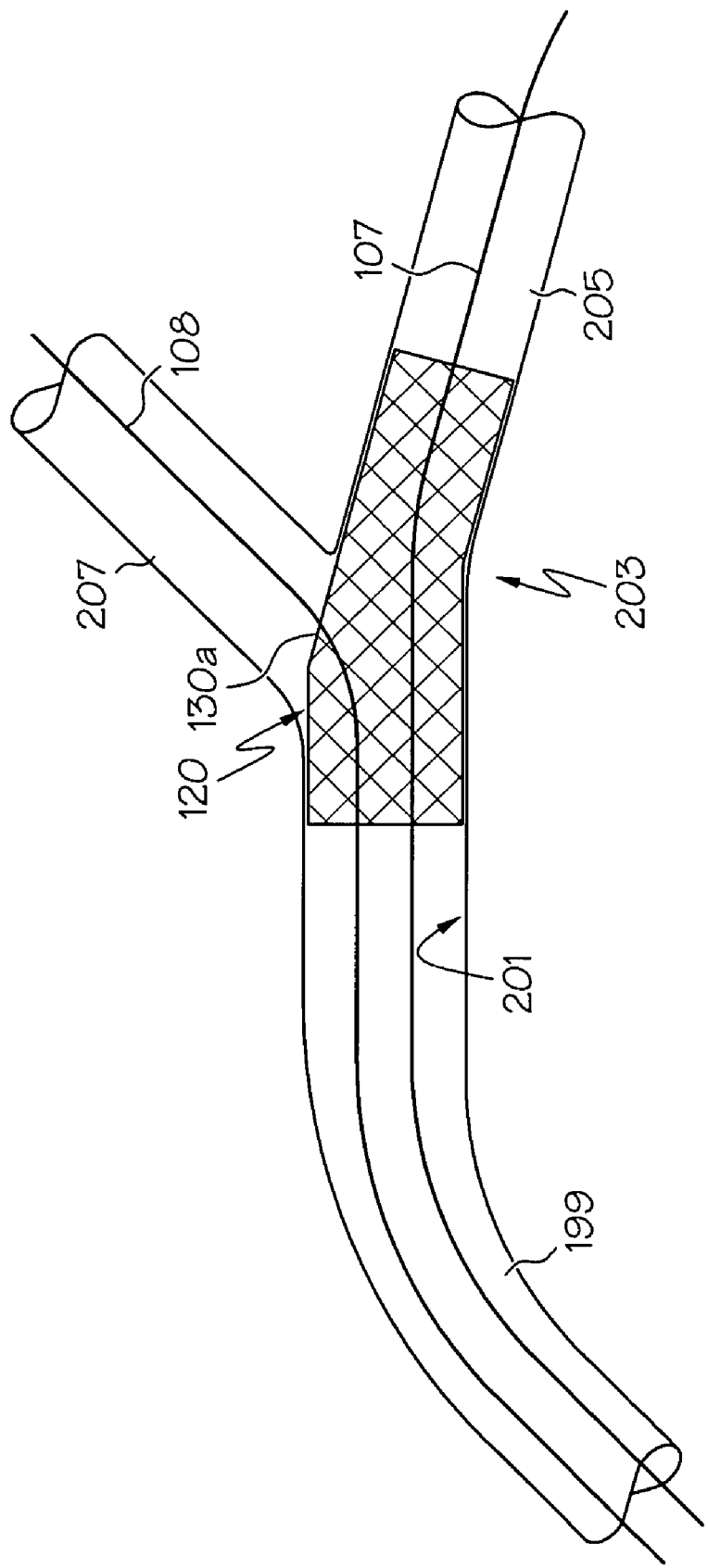
FIG. 9 is a side view of the stent depicted in FIG. 5, wherein the stent has been delivered from the catheter assembly, by balloon expansion and the assembly subsequently withdrawn from the vessel(s).

In at least one embodiment the stent 120, or one or more portions thereof, may be configured to deliver one or more therapeutic agents to a delivery site such as within the vessel 199 or one or more areas adjacent thereto, such as shown in FIGS. 5 and 9. In some embodiments one or stent members 132, such as is shown in FIG. 6, maybe configured to include one or more holes, notches, or other surface features to which one or more therapeutic agents 400 may be placed for delivery to the aneurysm site. A therapeutic agent may be placed on the stent in the form of a coating. In at least one embodiment the coating includes at least one therapeutic agent and at least one polymer.

A therapeutic agent may be a drug, a non-genetic agent, a genetic agent, etc. Some examples of suitable non-genetic therapeutic agents include but a re not limited to: anti-thrombogenic agents such as heparin, heparin derivatives, urokinase, and PPack (dextrophenylalanine proline arginine chloromethylketone); anti-proliferative agents such as enoxaprin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine and ropivacaine; anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters, vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin; bifunctional molecules consisting of an antibody and a cytotoxin; cholesterol-lowering agents; vasodilating agents; and agents which interfere with endogenous vascoactive mechanisms, and any combinations thereof.

Where an agent includes a genetic therapeutic agent, such a genetic agent may include but is not limited to: anti-sense DNA and RNA; DNA coding for anti-sense RNA, tRNA or rRNA to replace defective or deficient endogenous molecules; angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor; cell cycle inhibitors including CD inhibitors, thymidine kinase ("TK") and other agents useful for interfering with cell proliferation; at least one of the family of bone morphogenic proteins ("BMP's") such as BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Any of BMP-2, BMP-3, BMP-4, BMP-5, BMP-6 and BMP-7; dimeric proteins such as homodimers, heterodimers, or combinations thereof, alone or together with other molecules; molecules capable of inducing an upstream or downstream effect of a BMP such as "hedgehog" proteins, or the DNA's encoding them and any combinations thereof.

Where a therapeutic includes cellular material, the cellular material may include but is not limited to: cells of human origin (autologous or allogeneic); cells of non-human origin (xenogeneic) and any combination thereof. Some examples of cellular material include but are not limited to the following:

SP—(side population cells) These cells are thought to be some of the most primitive adult stem cells. They are isolated by a specific FACS technique utilizing the ability of SP cells to exclude Hoechst dye from the nucleus. In addition to bone marrow, SP cells have been isolated from most tissues, including: cardiac and skeletal muscle. By the more common surface protein identification these cells are Lin$^-$, Sca-1$^+$, c-Kit$^+$, CD43$^+$, CD45$^+$, CD34$^-$ Lin$^-$—(lineage negative cells) This group of cells is isolated from the bone marrow and all cells which have differentiated to a specific lineage (e.g. red blood cells) have been removed. Therefore leaving all of the stem and progenitor cells. This is beneficial because all primitive cells remain, but may reduce efficiency by including irrelevant, primitive cell types.

Lin$^-$CD34$^-$—Although CD34$^+$ cells have received much attention, many articles have been published lately which suggest the most primitive bone marrow derived stem cells are CD34$^-$ Lin$^-$CD34$^+$—Presence of the cell surface protein CD34 has been used to identify hematopoietic stem cells. However, the marker is also present on progenitor cells and white blood cells of various levels of maturity.

Lin$^-$cKit$^+$—cKit is the cell surface receptor for stem cell factor, and therefore a logical choice for stem cell selection. Most widely studied from bone marrow sources, but have also been isolated from the heart.

MSC—(mesenchymal stem cells) Named so because ordinarily these cells differentiate into cells of mesenchymal tissues (e.g. bone, cartilage, fat), but may also differentiate into cardiomyocytes under certain conditions. Easily isolated from bone marrow and, unlike hematopoietic stem cells, proliferate in vitro. A subpopulation of MSCs has been shown to self-renew faster and have a greater potential for multipotential differentiation than the general MSC population. D. Prockop from Tulane U. is publishing in this area.

Cord Blood Cells—Derived from the blood remaining in the umbilical vein following child birth. This blood has been shown to contain a higher percentage of immature stem cells or progenitor cells. Typically, a matched donor must be found for patients, but a lower incidence of graft versus host disease compared to stem cell isolation from adult blood has been reported. Disadvantages include: insufficient cell number in small blood volumes, unforeseen congenital defects, and contamination by mother's blood which is likely not HLA matched.

Cardiac or other tissue derived stem cells—Most work to date has focused on isolating stem cells from bone marrow. This is due to extensive work in improving bone marrow transplants for chemotherapy and leukemia treatments. However, there is evidence that similar stem cells which can be identified by similar means (e.g. SP, cKit) can be isolated from other tissues (e.g. fat, cardiac muscle).

Whole bone marrow—An "it's in there" approach where whole bone marrow (filtered for bone particles) is transplanted. Benefits include: little processing, all stem and progenitor cells are present, and matrix proteins and growth factors may also be present. Downside—if one or two stem cell types are responsible for cardiac improvement they will only be present in very low numbers.

BM-MNCs—(bone marrow mononuclear cells) Separated from whole bone marrow by a density gradient centrifugation procedure, this population contains non-granular white blood cells, progenitor cells, and stem cells.

EPCs—(endothelial progenitor cells) isolated from bone marrow based on cell surface markers, these cells will become endothelial cells. In theory, these cells will form new blood vessels when delivered to ischemic tissue.

Skeletal myoblasts—(or satellite cells) These cells are responsible for the regeneration of skeletal muscle following injury. They have the ability to fuse with other myoblasts or damaged muscle fibers. Cardiac muscle therapies assume these cells can integrate into the host tissue and improve tissue properties or functionally participate in contraction.

MDCs—(muscle derived cells) A population of cells isolated from adult skeletal muscle which are similar to myoblasts. The isolation technique preplating entails collecting cells which attach to culture dishes at different times after biopsy. Cells with the best potential plate in the $6^{th}$ group and takes several days to obtain. Investigators working with these cells claim they are a refined population of myoblasts and should result in higher engraftment efficiencies and efficacious procedures.

Go cells—Recently isolated from adult skeletal muscle, these non-satellite cells express GATA-4 and, under certain in vitro growth conditions, progress to spontaneously beating cardiomyocyte-like cells.

Endothelial cells—Transplantation of autologous endothelial cells along with a fibrin matrix induced angiogenesis and improved cardiac function in an ischemic sheep model.

Adult cardiomyocytes

Fibroblasts—Easily obtained from adult tissues, fibroblasts may provide growth factors or participate in the would healing response. Fibroblast play a critical role in wound healing; the synthesis and deposition of extracellular matrix. Fibroblasts commonly become contractile in wound healing environments.

Smooth muscle cells—Isolated from arteries, these cells may participate or encourage angiogenesis and/or beneficial cardiac remodeling following MI.

MSCs+5-aza—Culture of mesenchymal stem cells with 5-aza forces differentiation into cardiomyocytes. These cells beat spontaneously after treatment.

Adult cardiac fibroblasts+5-aza—In theory, in vitro treatment of cardiac fibroblasts with 5-aza will result in differentiation into myogenic cells.

Genetically modified cells—Isolation of cells from the patient and genetically modifying them in vitro to encourage production of proteins or differentiation into a cell type which will be beneficial for treating heart failure.

Tissue engineered grafts—Isolation of cells from the patient which are then seeded onto and cultured within resorbable scaffolds (e.g. collagen, PLGA). These cell seeded constructs are then implanted into the patient.

MyoD scar fibroblasts—MyoD family of transcription factors prompt skeletal muscle cell differentiation in fibroblasts. Procedure involves isolation of cardiac scar fibroblasts, genetic transfection with MyoD in vitro and delivery of the cells to the heart to encourage myogenesis.

Pacing cells—Genetically modified fibroblasts which become electrically conducting and signal generators.

Embryonic stem cell clones—Use of cloning technology to produce cardiomyocytes, progenitors, or stem cells which are genetically identical to the patient.

Embryonic stem cells—These cells are the most primitive of cells and will differentiate into functional cardiomyocytes under certain conditions. Both political and technological hurdles must be overcome before commercialization of this technology.

Fetal or neonatal cells—Isolated from the heart of donors, these cells may incorporate into host tissue without immune rejection. Some cardiomyocyte progenitor cells must be present due to the continued growth of the heart in fetal and neonatal humans.

Immunologically masked cells—Allogeneic cell sources (e.g. donor cardiomyocytes) are currently unfeasible due to immune rejection. However, masking technologies have been developed which could make this technology feasible.

Tissue engineered grafts—Isolation of cells from a donor which are then seeded onto and cultured within resorbable scaffolds (e.g. collagen, PLGA). These cell seeded constructs are then implanted into the host or recipient.

Genetically modified cells—Isolation of cells from a donor and genetically modifying them in vitro to encourage production of proteins or differentiation into a cell type which will be beneficial for treating heart failure. The modified cells will then be transplanted into the host or patient.

Teratoma derived cells—A teratocarcinoma is a form of cancer in which the tumor is composed of a heterogeneous mixture of tissues. Through isolation of cells from this tumor and in vitro manipulation and culture a neuronal cell line has been developed. Layton Biosciences has successfully used these cells to form new brain tissue in stroke patients. Similar techniques may be used to produce a myogenic cell line.

Where a therapeutic agent comprises at least one polymer agent or coating, the at least one coating may include but is not limited to: polycarboxylic acids; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers such as EVA; polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; proteins; polypeptides; silicones; siloxane polymers; polylactic acid; polyglycolic acid; polycaprolactone; polyhydroxybutyrate valerate and blends and copolymers thereof; coatings from polymer dispersions such as polyurethane dispersions (BAYHDROL®, etc.), fibrin, collagen and derivatives thereof; polysaccharides such as celluloses, starches, dextrans, alginates and derivatives; hyaluronic acid; squalene emulsions; polyacrylic acid, a copolymer of polylactic acid and polycaprolactone; medical-grade biodegradable materials such as PGA-TMC, Tyrosine-Derived Polycarbonates and arylates; polycaprolactone co butyl acrylate and other co polymers; Poly-L-lactic acid blends with DL-Lactic Acid; Poly(lactic acid-co-glycolic acid); polycaprolactone co PLA; polycaprolactone co butyl acrylate and other copolymers; Tyrosine-Derived Polycarbonates and arylate; poly amino acid; polyphosphazenes; polyiminocarbonates; polydimethyltrimethylcarbonates; biodegradable CA/PO$_4$'s; cyanoacrylate; 50/50 DLPLG; polydioxanone; polypropylene fumarate; polydepsipeptides; macromolecules such as chitosan and Hydroxylpropylmethylcellulose; surface erodible material; maleic anhydride copolymers; zinc-calcium phosphate; amorphous polyanhydrides; sugar; carbohydrate; gelatin; biodegradable polymers; and polymers dissolvable in bodily fluids; and any combinations thereof.

In at least one embodiment an example of a suitable polymer agent or coating comprises block copolymers comprising at least one A block and at least one B block. The A blocks are preferably soft elastomeric blocks, which are based upon one or more polyolefins, or other polymer with a glass transition temperature at or below room temperature. For example, the A blocks can be polyolefinic blocks having alternating quaternary and secondary carbons of the general formulation: —(CRR'—CH$_2$)$_n$—, where R and R' are, independently, linear or branched aliphatic groups such as methyl, ethyl, propyl, isopropyl, butyl, isobutyl and so forth, or represent cyclic aliphatic groups such as cyclohexane, cyclopentane, and the like, either with or without pendant groups. Preferred polyolefinic blocks include polymeric blocks of isobutylene,

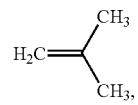

(i.e., polymers where R and R' are methyl groups). Other examples of A blocks include silicone rubber blocks and acrylate rubber blocks.

The B blocks are preferably hard thermoplastic blocks with glass transition temperatures significantly higher than the elastomeric A blocks which, when combined with the soft A blocks, are capable of, inter alia, altering or adjusting the hardness of the resulting copolymer to achieve a desired combination of qualities. Examples of B blocks include polymers of methacrylates or polymers of vinyl aromatics. More specific examples of B blocks include blocks that are (a) formed from monomers of styrene

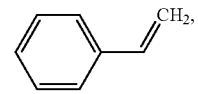

styrene derivatives (e.g., α-methylstyrene, ring-alkylated styrenes or ring-halogenated styrenes or other substituted styrenes where one or more substituents are present on the aromatic ring) or mixtures of the same, collectively referred to herein as "styrenic blocks" or "polystyrenic blocks" or are (b) formed from monomers of methylmethacrylate, ethylmethacrylate, hydroxyethyl methacrylate or mixtures of the same.

The block copolymers are provided in a variety of architectures, including cyclic, linear, and branched architectures. Branched architectures include star-shaped architectures (e.g., architectures in which three or more chains emanate from a single region), comb architectures (e.g., copolymers having a main chain and a plurality of side chains), and dendritic architectures (including arborescent or hyperbranched copolymers).

Some specific examples of such block copolymers include the following: (a) BA (linear diblock), (b) BAB or ABA (linear triblock), (c) B(AB)$_n$ or A(BA)$_n$ (linear alternating block), or (d) X-(AB)$_n$ or X-(BA)$_n$ (includes diblock, triblock and other radial block copolymers), where n is a positive whole number and X is a starting seed, or initiator, molecule. One specific group of polymers have X-(AB)$_n$ structures, which are frequently referred to as diblock copolymers and triblock copolymers where n=1 and n=2, respectively (this terminology disregards the presence of the starting seed molecule, for example, treating A-X-A as a single A block, with the triblock therefore denoted as BAB). A particularly beneficial polymer from this group is polystyrene-polyisobutylene-polystyrene triblock copolymer (SIBS). Where n=3 or more, these structures are commonly referred to as starshaped block copolymers. Other examples of block polymers include branched block copolymers such as dendritic block copolymers, wherein at least one of the A and B blocks is branched, for instance, where the A blocks are branched and are capped by the B blocks.

Once the stent 120 is positioned on the assembly 100, such as in the manner shown in FIG. 2, the assembly 100 may be slid onto a catheter 116, such as is shown in FIGS. 3–4 so that the sheath 102 is rotatingly disposed about the balloon 114 and a proximal portion 140 of the secondary guidewire housing 104 is engaged to a rotating collar 150.

The collar 150 is engaged to the proximal portion 140 of the secondary guidewire housing 104 by any engagement mechanism desired, such as welding, bonding, mechanical engagement, adhesive engagement, etc. In the embodiments shown in FIG. 4 for example, the proximal portion 140 of the secondary guidewire housing 104 and the collar 150 are engaged externally at engagement site 142. In some embodiments the secondary guidewire housing 104 may be passed at least partially through the collar 150, and/or the collar 150 may define a lumen through which the secondary guidewire 108 may be passed before entering into the secondary guidewire housing 104.

Collar 150 may be a substantially cylindrical member that is disposed about the shaft 144 of the catheter 116 at a position proximal of the balloon 114. The collar 150 may be characterized as defining a catheter shaft lumen 146 through which the catheter shaft 144 is passed. In order to provide the collar 150 with the ability to freely rotate about the catheter shaft 144, the collar 150 defines a catheter shaft lumen 146 which has a diameter greater than the outer diameter of the shaft 144. In some embodiments one or more lubricious substances may be placed between the collar 150 and the shaft 144 to further encourage free rotation therebetween.

While the rotating collar 150 is free to rotate about the shaft 144, in some embodiments it will also be capable of being longitudinally displaced along the shaft 144 as well. As such, in some embodiments one or more locks or hubs 152 may be affixed about the shaft 144 on one or both sides of the collar 150 to prevent or limit the potential longitudinal displacement of the collar 150 relative to the shaft 144.

As is shown in FIG. 5, when the assembly 100, including the stent 120 is placed on the catheter 116, the combined system 300 is ready for use in a stent delivery procedure. However, in some cases it may be necessary to provide the system 300 with one or more stent retaining elements to retain or aid in retaining the stent in place about the sheath 102. In light of the above, however, such elements must be configured so as to not unduly interfere with the rotatability of the assembly 100 about the catheter 116.

In at least one embodiment, an example of which is shown in FIG. 10 the stent delivery system 300 includes a pair of retaining and/or protective sleeves 170 and 172. The sleeves may be constructed from any of a variety of materials such as are described in U.S. Pat. No. 6,443,980; U.S. Pat. No. 6,221,097; U.S. Pat. No. 6,554,841; U.S. 6,733,520; and U.S. Pub. App. No. 2002-0038140 A1, and U.S. Pub. App. No. 2002-0038141 A1, the entire content of each of which are incorporated herein by reference, but are typically constructed of one or more polymeric and/or elastomeric materials.

Sleeves 170 and 172 may function to retain the ends of the balloon 114 in a reduced state prior to delivery and/or to aid in deflation and collapse of the balloon 114 following delivery of the stent by providing a radially inward acting force on the ends of the balloon 114. As is shown in FIG. 10, the sleeves 170 and 172 may be provided with a sufficient length to allow a first portion 178 of each sleeve to be disposed over a respective proximal end portion 174 and/or distal end portion 176 of the stent 120.

Figure 13:
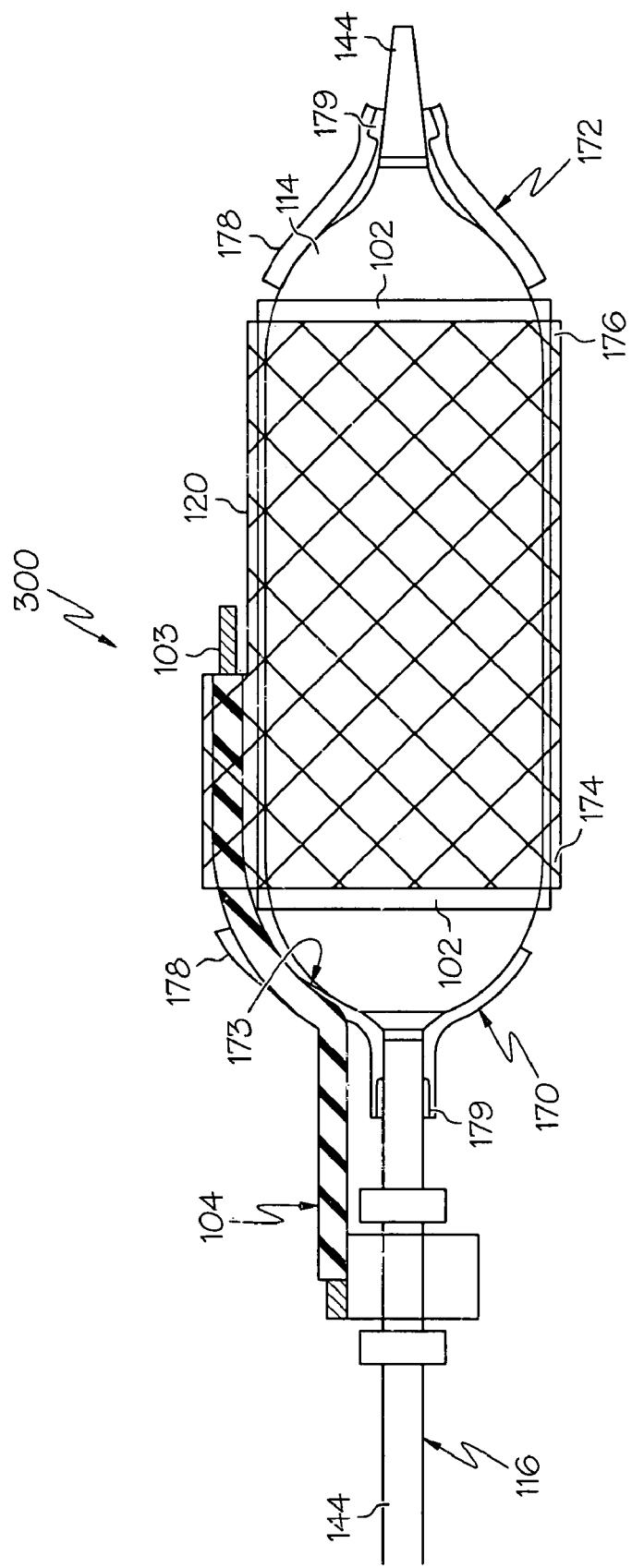
FIG. 13 is a side view of the embodiment shown in FIG. 10 wherein the sleeves have been retracted from the ends of the stent.

When the balloon 114 is expanded to deliver the stent 120, such as is shown in FIG. 13, the increased diameter of the balloon 114 and/or stent 120 cause the first portion 178 of each sleeve 170 and 172 to be retract or be pulled off of the end portions 174 and 176 of the stent 120, thereby freeing the stent for delivery from the system 300.

Though sleeves 170 and 172 aid in retaining the stent and/or balloon in an unexpanded or pre-delivery state, the each sleeve is also rotatable about the catheter shaft 144, in a manner similar to that of the sheath 102. In order to provide the sleeves with the capacity to rotate, a second portion of each sleeve, corresponding to the portion of the sleeve engaged to the catheter shaft 144, comprises a rigid reinforcing member 179 that is rotatably engaged about the catheter shaft 144.

The rigid reinforcing member 179 may be constructed out of any material or materials having a higher durometer value than that of the material or materials from which the retaining or first portion 178 is constructed. As a result the sleeves 170 and 172 will have a hybrid construction of at least two materials having different hardnesses.

In some embodiments it may be desirable to provide only the distal end of the system 300 with a sleeve 172. Where the system employs a proximal sleeve 170, the proximal sleeve includes an opening 171, such as is best depicted in FIGS. 11 and 12, to accommodate passage of the secondary guidewire housing 104 therethrough. When the balloon 114 and stent 120 are expanded in the manner shown in FIG. 13, the proximal sleeve 170 may be drawn proximally along the secondary guidewire housing 104 and off of the proximal end portion 174 off the stent 120. To encourage ease of retraction, at least a portion of the inside surface 173 of one or both sleeves may be at least partially coated with a lubricious substance.

Figure 14:
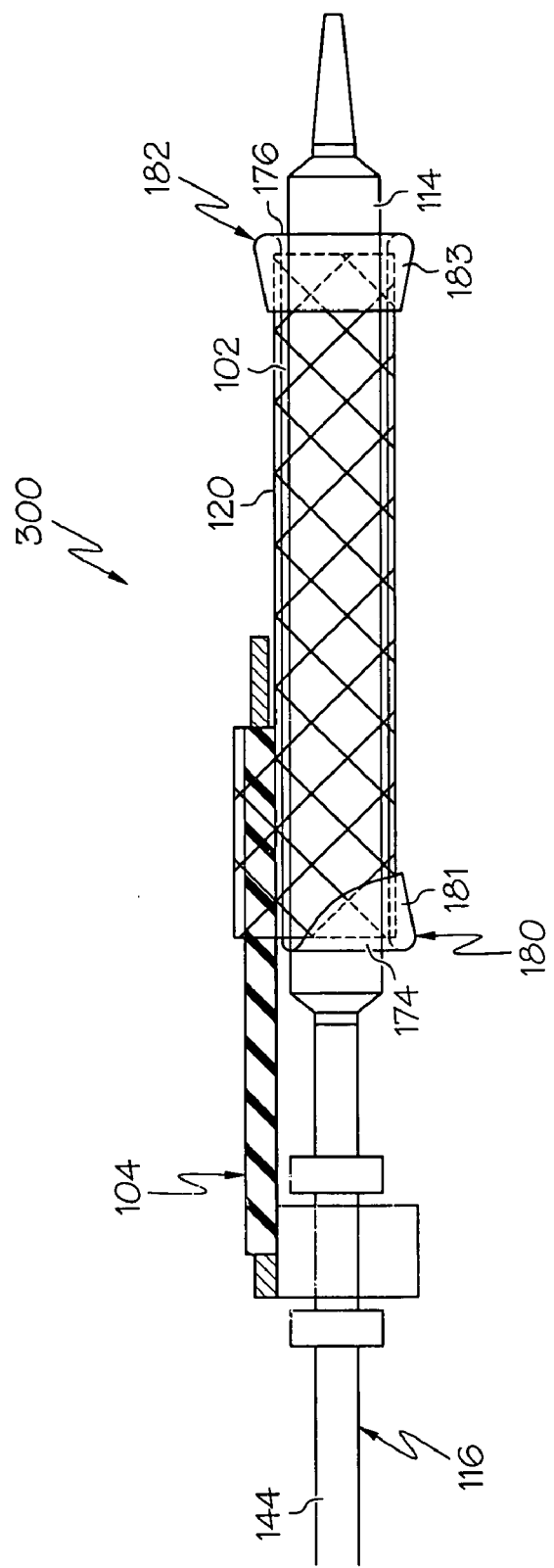
FIG. 14 is a side view of an embodiment of the invention wherein each end of the rotating sheath is folded over the corresponding end of the stent.

In some embodiments the balloon 114 is sufficiently folded or otherwise maintained in the unexpanded configuration, such that providing a sleeve or other protective/retaining means over the ends of the balloon is unnecessary and/or undesirable. However, it may still be desirous to cover, or otherwise protect, one or more end portions 174 and 176 of the stent 120. As such, in at least one embodiment of the invention, an example of which in show in FIG. 14, the rotatable sheath 102 includes one or two end portions 180 and 182, which extend beyond the corresponding end portions 174 and 176 of the stent 120. The end portions 180 and 182 comprise flaps 181 and 183, which are configured to be folded or rolled back over the corresponding end portion 174 and 176 of the stent 120, while in the stent is in the unexpanded or pre-delivery state.

Due the to presence of the secondary guidewire housing 104, in some embodiments the only the distal end portion 176 of the stent is overlapped by a distal flap 182 of the sheath 102. However, in some embodiments a proximal flap 181 may have any of a variety of configurations to provide at least partial coverage of the proximal end portion 174 of the stent 120 in the unexpanded state. For example, in FIG. 14 a proximal flap 181 is provided with a tapered shape which allows the flap to be folded back with an angled configuration to a provide the proximal end portion 174 of the stent 120 with complete or nearly complete coverage in the region opposite from the secondary guidewire housing 104. As the folded flap 181 approaches the region of the secondary guidewire housing 104 the coverage of the proximal end portion of the stent 120 by the flap 181 is reduced in the tapering manner shown.

Figure 15:
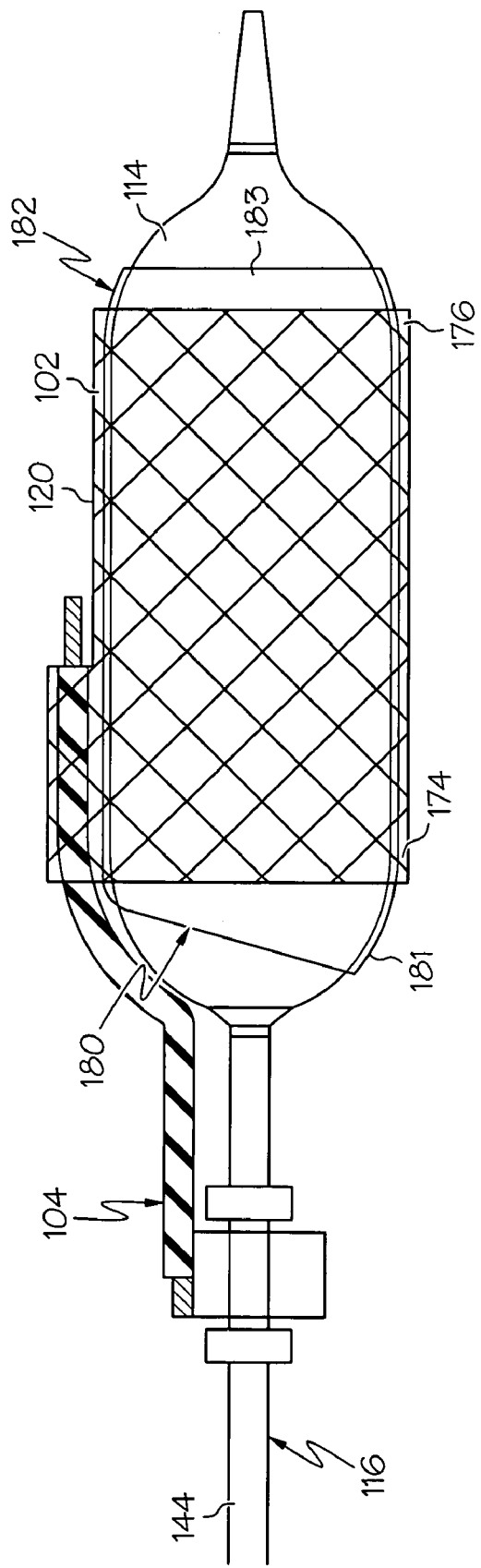
FIG. 15 is a side view of the embodiment shown in FIG. 14, wherein the ends of the sheath have been retracted off of the stent.

When the stent 120 is expanded, such as in the manner shown in FIG. 15, the flaps 181 and 183 of the sheath 102 will slide off of the respective end portions 174 and 176 of the stent 120 to free the stent for delivery. In some embodiments the flaps 181 and 183 may be configured to exert an inwardly acting radial force upon the ends of the balloon 114 following delivery of the stent 120, in order to encourage the balloon to refold or fully collapse for withdrawal from the body.

Figure 16:
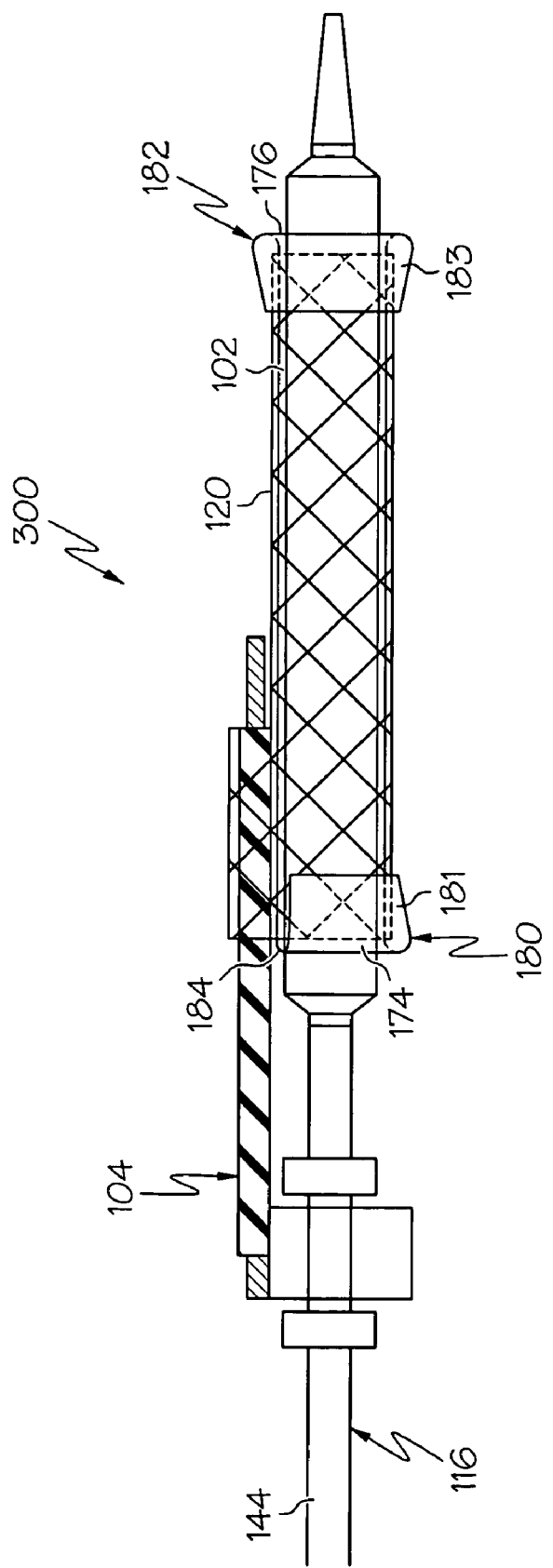
FIG. 16 is a side view of an embodiment of the invention wherein each end of the rotating sheath is folded over the corresponding end of the stent and the proximal end of the sheath defines a slot.
Figure 17:
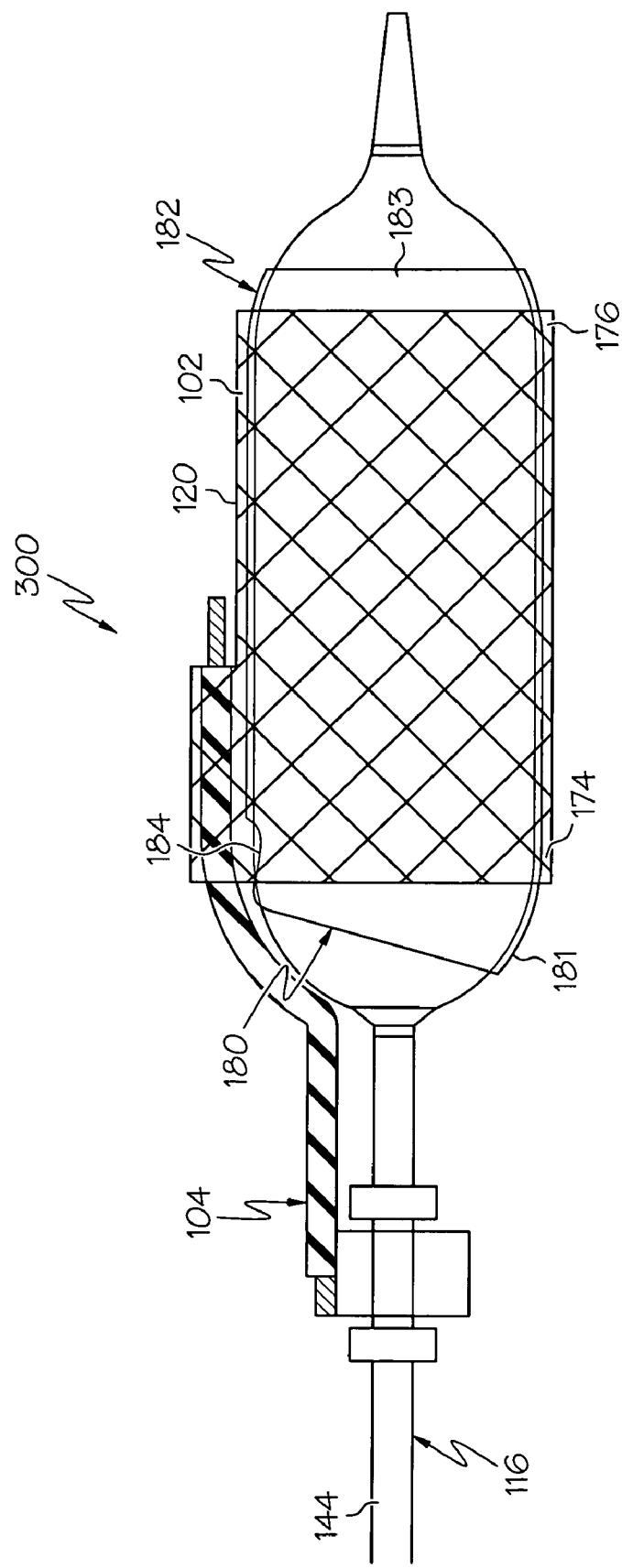
FIG. 17 is a side view of the embodiment shown in FIG. 16, wherein the ends of the sheath have been retracted off of the stent.

In some embodiments, the proximal flap 181 may define a slot or opening 184, such as is shown in FIGS. 16 and 17. Slot 184 allows the flap 180 to be folded back over the proximal end portion 174 of the stent 120 to provide a uniform length of coverage to the stent, excepting the region of the stent 120 wherein the secondary guidewire housing 104 is positioned. In some embodiments it may be desirable to provide the system 300 with a balloon 114 and/or stent 120 that tends to initially expand initially at a center region to encourage the flaps 180 and 182 to fully retract from the stent; such balloons 114 and stents 120 are known.

In the various embodiments, shown in FIGS. 14–17, at least a portion of the stent side surface of the flaps 181 and 183 and/or the corresponding end portions 174 and 176 of the stent 120 may include a lubricious coating thereon to encourage the sliding retraction of the flaps from the stent during expansion.

Figure 18:
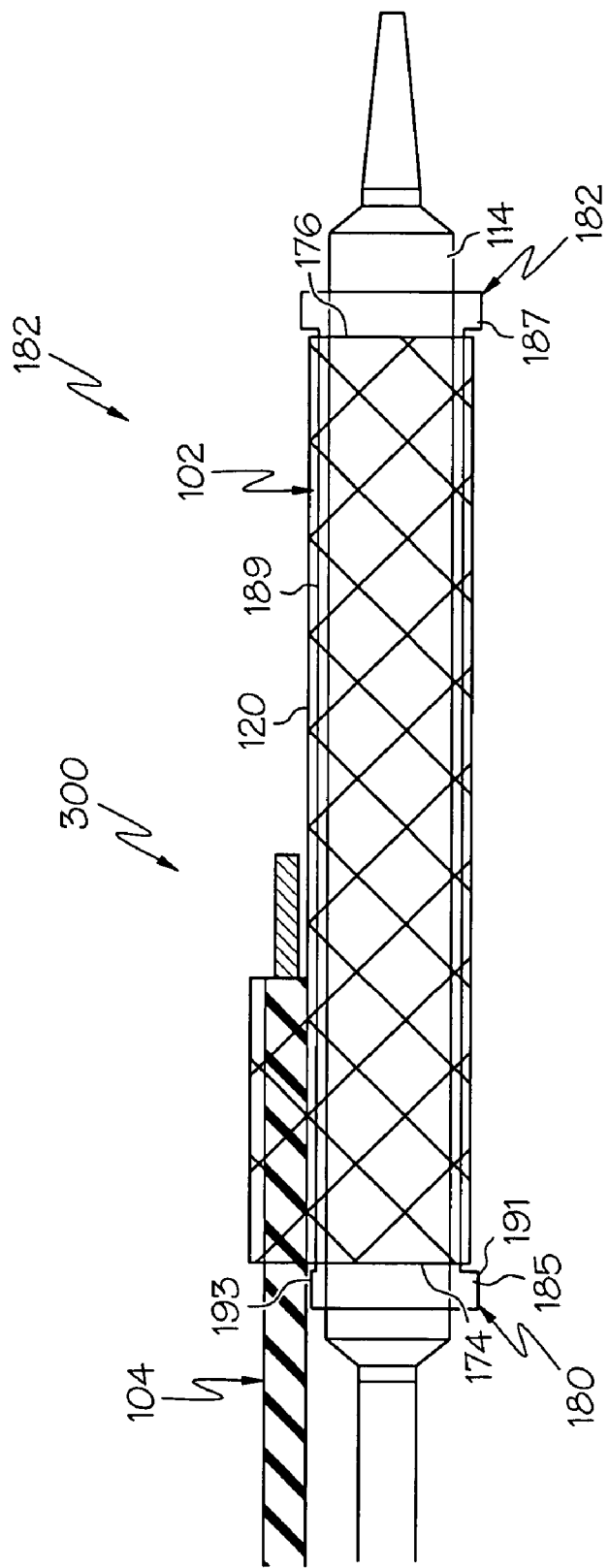
FIG. 18 is a side view of an embodiment of the invention wherein the rotating sheath comprises a pair raised end portions or hubs.
Figure 19:
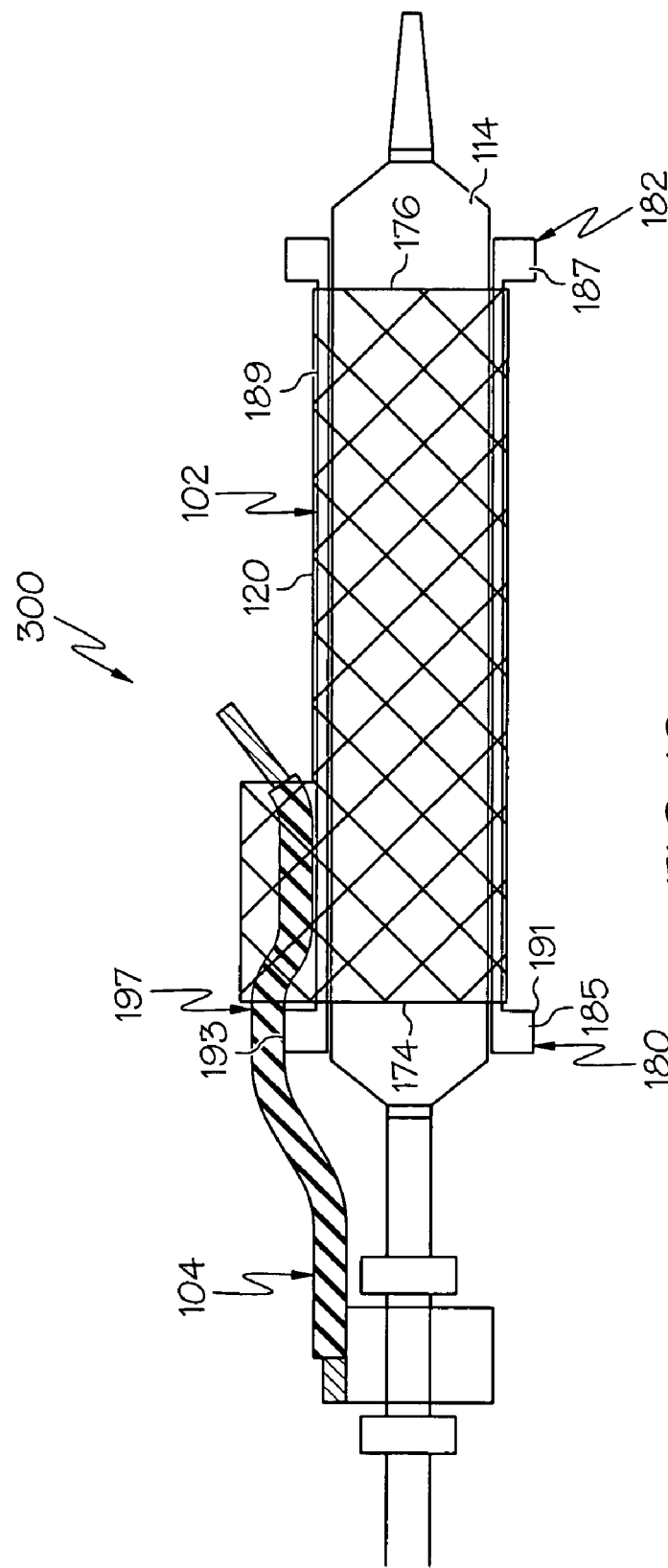
FIG. 19 is a side view of an embodiment of the invention shown in FIG. 18 wherein the secondary guidewire housing comprises a bent portion over the proximal hub of the rotating sheath.

Rather than configuring the sheath 102 to have end portions 180 and 182 which can be folded back over the corresponding end portions 174 and 176 of the stent 120, in some embodiments, an example of which is shown in FIGS. 18 and 19, the end portions 180 and 182 of the sheath define hub regions 185 and 187 which have a greater outside diameter than the stent mounting region 189 of the sheath positioned therebetween.

When a stent 120 is mounted in the relatively recessed area of the stent mounting region of the sheath 102, the outer diameter of a distal hub 187 is equal to or greater than the outer diameter of the distal end portion 176 of the stent 120 in the unexpanded state. While in some embodiments the sheath 102 is provided with only a distal hub 187, in some embodiments a proximal hub 185 is also included.

In some embodiments, such as those shown in FIGS. 18 and 19 the proximal hub 185 underlies or is adjacent to the secondary guidewire housing 104. This configuration provides the proximal hub 185 with a shape wherein only a "bottom" portion 191 of the proximal hub 185 has an outer diameter greater than that of the stent 120 and a "top" portion 193 of the hub 185 being adjacent to the secondary guidewire housing 104. In some embodiments the secondary guidewire housing 104 may be bonded, adhered, fused or otherwise engaged to the proximal hub 185.

In some embodiments, an example of which is shown in FIG. 19 the secondary guidewire housing 104 may be utilized to protect the area of the proximal end portion 174 of the stent not protected by the top portion of the hub 185. In such embodiments the secondary guidewire housing 104 may include a bent portion 197 which bends around the proximal hub 185 of the sheath 102 prior to passage through the stent 120. This bent portion 197 effectively adds its diameter to that of the proximal hub 185, such that the bent portion 197 extends radially outward to a greater extent than the proximal end portion 174 of the stent 120. As a result, the proximal end portion 174 of the stent 120 is uniformly protected by the combination of the hub 185 and bent portion 197 of the secondary guidewire housing 104.

Figure 20:
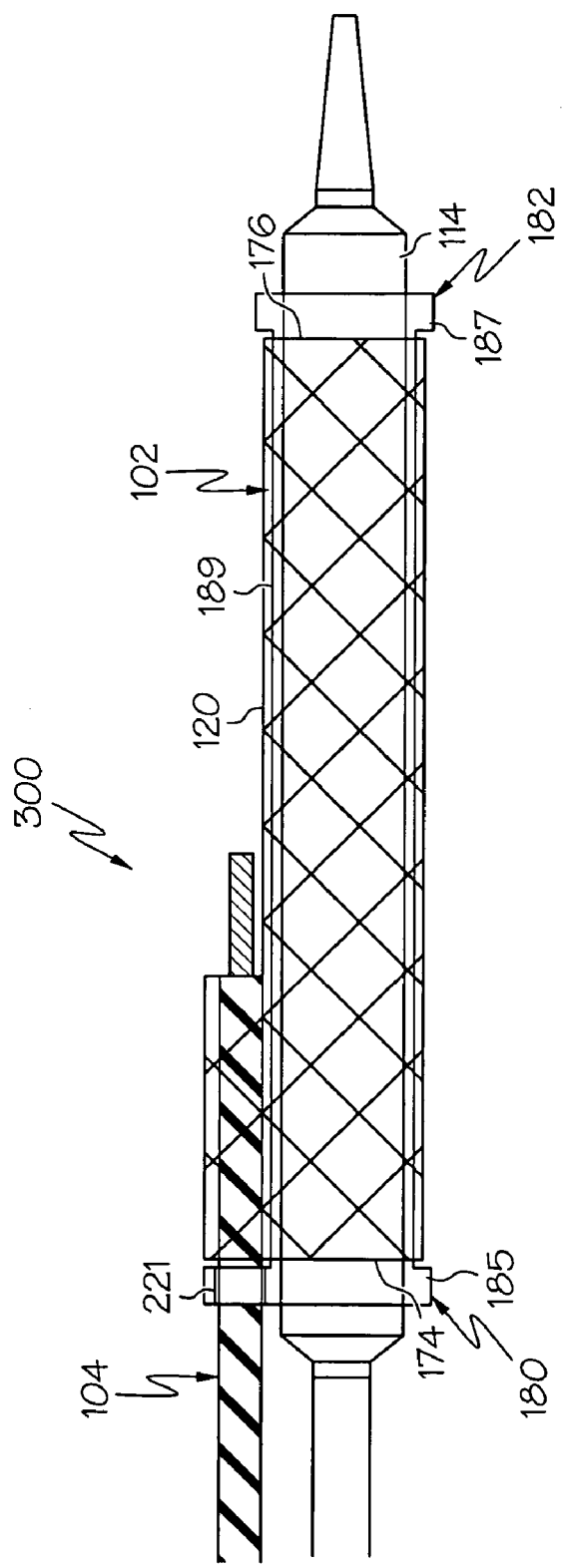
FIG. 20 is a side view of an embodiment of the invention wherein the rotating sheath comprises a pair raised end portions or hubs, wherein the proximal hub defines a passage for the secondary guidewire housing.

In some embodiments, an example of which is shown in FIG. 20, the proximal hub 185 defines an opening 221, through which the secondary guidewire housing 104 passes. In this embodiment the proximal hub 185 may be shaped and sized to have a diameter that is uniformly larger, or at least equal to, the diameter to the proximal end portion 174 of the stent 120 in the unexpanded state. In embodiments where the secondary guidewire housing 104 passes through opening 221, the housing 104 will be inherently confine by the hub 185 eliminating any need to bond the housing 104 to the hub 185.

In the various embodiments of the inventions described above, or alternatively therefrom, the secondary guidewire housing 104 may be configured to provide the proximal end 174 of the stent 120 with improved edge protection and/or coverage. For example, in the embodiment shown in FIG. 21, rather than extending the hypotube 64 through the secondary opening 130a of the stent 120, the hypotube 64 terminates adjacent to the proximal end portion 174 of the stent 120. The hypotube 64 may be configured such that a portion of the hypotube 64 is positioned so that it extends radially outward from the system to an extent equal to or greater than the adjacent region of the proximal end portion 174 of the stent 120.

In some embodiments the entire secondary guidewire housing 104 is positioned proximally adjacent to the stent 120 such that the secondary guidewire 108 exits the housing 104 and passes freely through the secondary opening 130a of the stent 120.

To retain the hypotube 64 in a position such that it protects the proximal end portion 174 of the stent 120 in the manner shown in FIG. 21, and described above, the hypotube 64 encloses the inner shaft 103 in an asymmetrical relationship, such as is depicted in the cross-sectional view of FIG. 22.

Figure 23:
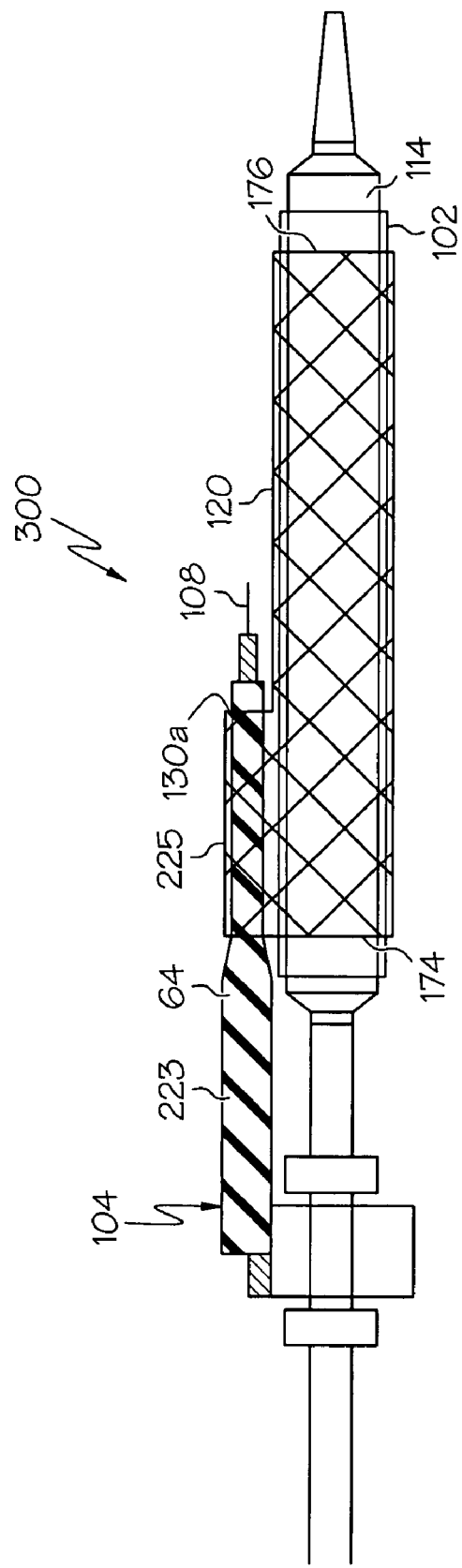
FIG. 23 is a side view of an embodiment of the invention wherein the secondary guidewire housing comprises a step which is radially offset from the proximal end of the stent.

In some embodiments, an example of which is shown in FIG. 23, the hypotube 64 may be tapered or provided with a stepped configuration where it enters under the proximal end portion 174 of the stent 120. In the embodiment show a portion of the hypotube 64 proximal to the stent 120 is displaced relative to the stent 120, such that a proximal portion 223 of the hypotube 64 extends radially outward from the system to an extent equal to or greater than the adjacent region of the proximal end portion 174 of the stent 120. A distal portion 225 of the hypotube 64 which extends from the proximal portion 223 tapers or steps down to a reduced diameter portion which extends through the secondary opening 130a of the stent 120.

Figure 24:
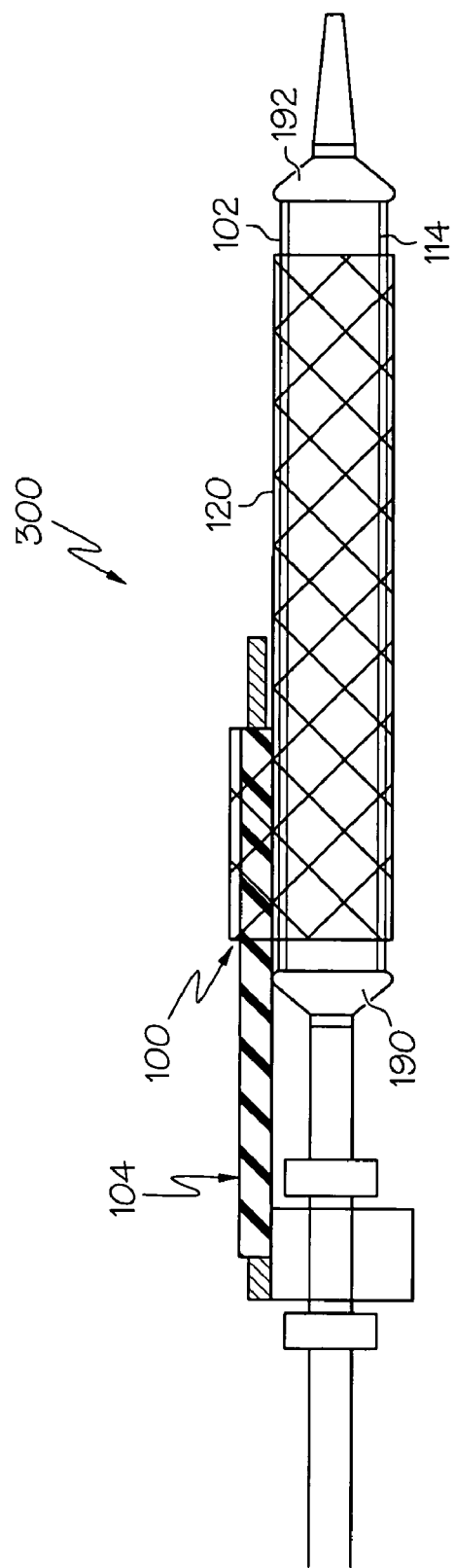
FIG. 24 is a side view of an embodiment of the invention wherein the cones of the balloon are provided with a puffed configuration in the unexpanded state.
Figure 25:
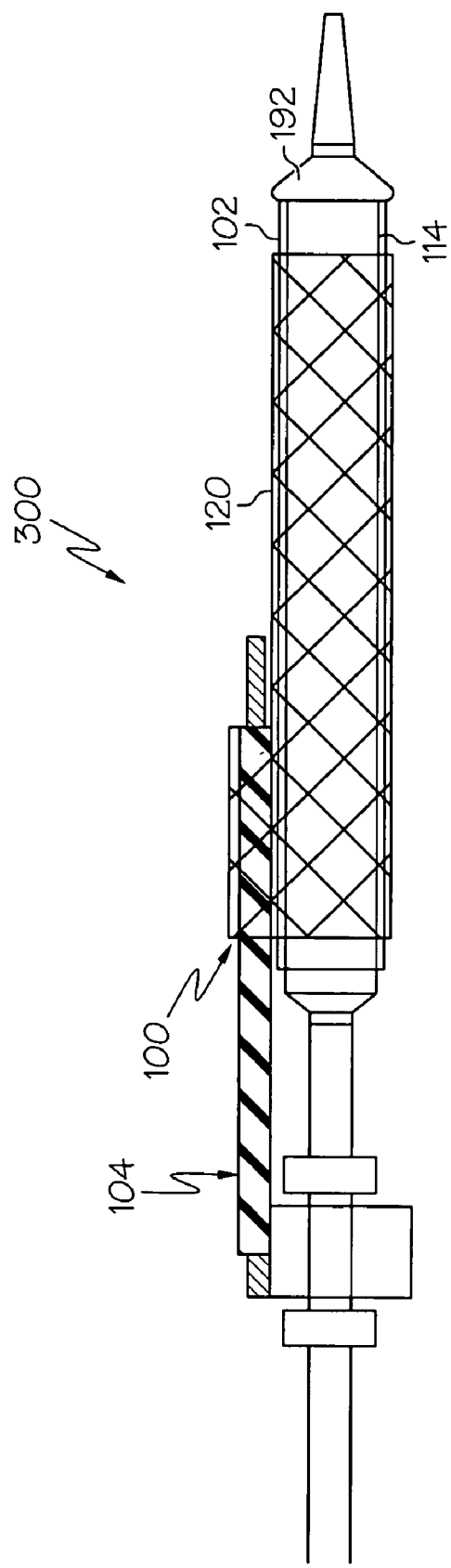
FIG. 25 is a side view of an embodiment of the invention wherein only the distal cone of the balloon is provided with a puffed configuration in the unexpanded state.
Figure 26:
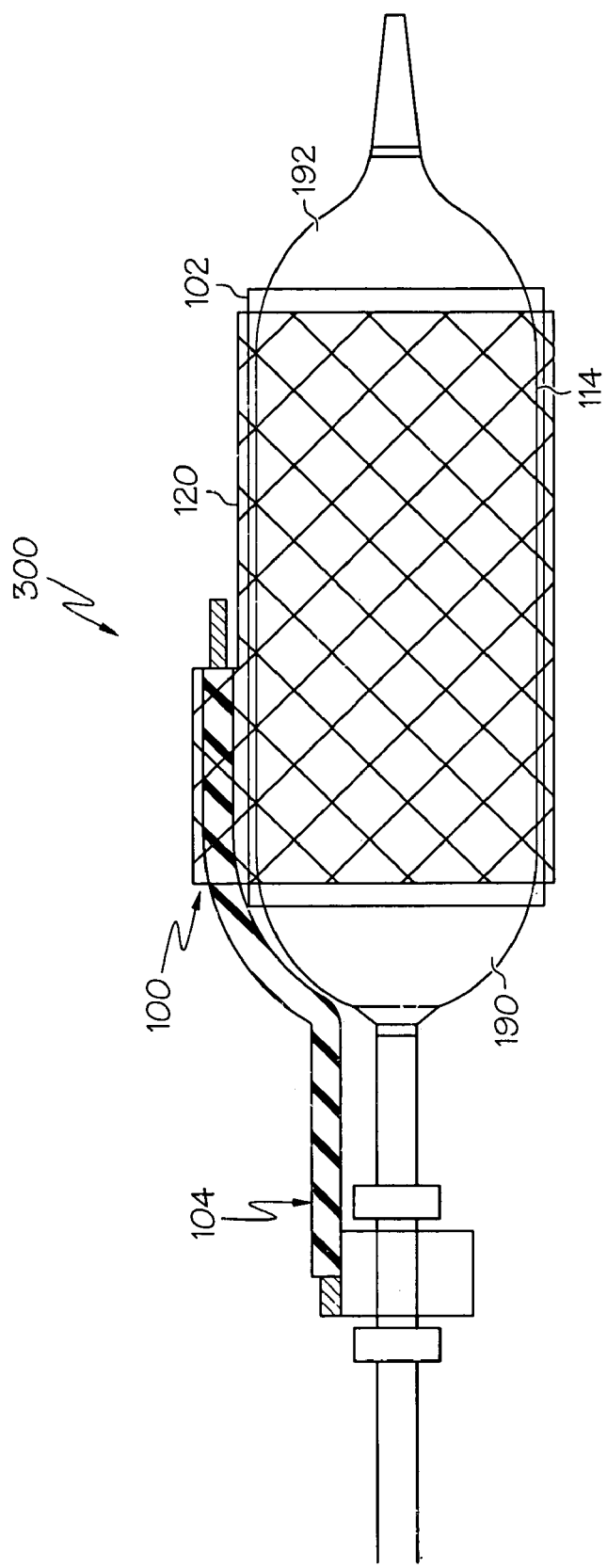
FIG. 26 is a side view of either of the embodiments shown in FIGS. 24 and 25, wherein the balloon is shown in an expanded state.

In some embodiments of the invention, one or both cones 190 and 192 of the balloon 114 may have a "puffed" configuration, such that in the unexpanded state, at least a portion of one or both cones 190 and 192 have a diameter greater than the outside diameter of the sheath 102 and/or stent 120 mounted on the balloon 114, such as shown in FIG. 24. In the expanded state, shown in FIG. 26, the cones have a diameter less than that of the stent 120. In the embodiment shown in FIG. 25 only the distal cone 192 is provided with a puffed configuration.

The puffed configuration of the cones 190 and 192, shown in FIG. 24 further protects the assembly 100 from longitudinal displacement relative to the catheter 116 during advancement, and provides the stent 120 with similar protection relative to the sheath 102. In keeping with the principles described herein, one or both puffed cones are configured such that they do not interfere with the rotatability of the sheath 102 about the balloon 114 when in the unexpanded state.

It will be recognized that the cones 190 and 192 of a balloon 116 may be provided with the puffed configuration shown in a variety of ways. For example, following assembly of the system 300 fluid may be evacuated from the balloon 114 while one or both cones 190 and 192 are exposed to vacuum, thereby allowing the balloon 114 to attain its folded pre-delivery configuration while simultaneously causing the cones to be distorted or shaped into the puffed configuration shown in FIG. 24. Alternatively, the portion of the balloon 114 that underlies the sheath 102 may be externally retained in the unexpanded state, while fluid is injected into the balloon 116 causing the cones to expand. The cones may be expanded to a degree sufficient to distort the cones 190 and 192 into the puffed configuration shown. It is recognized that other methods of providing one or both cones 190 and 192 with the puffed configuration shown in FIGS. 24 and 25 and such methods are within the scope of the invention.

The invention has been described with reference to the embodiments. Obviously, modifications and alterations will occur to others upon a reading and understanding of this specification. For example, the illustrated embodiments use a balloon to expand the stent although, as briefly noted above, a self expanding, self deploying or hybrid expandable stent can be used without departing from the features of the present invention. The invention is intended to include all such modifications and alterations thereof.

Furthermore, it is noted that the various embodiments shown and described in U.S. patent application Ser. No. 10/375,689, filed Feb. 27, 2003 and U.S. patent application Ser. No. 10/657,472, fied Sep. 8, 2003, both of which are entitled Rotating Balloon Expandable Sheath Bifurcation Delivery, may be incorporated and/or utilized with the various embodiments described herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

With this description, those skilled in the art may recognize other equivalents to the specific embodiment described herein. Such equivalents are intended to be encompassed by the claims attached hereto.

The invention claimed is:

1. A catheter assembly comprising:
a catheter, the catheter comprising a catheter shaft and a balloon disposed about a distal region of the catheter shaft, the balloon being expandable from and between a reduced diameter configuration and an expanded diameter configuration;
a rotatable sheath, the rotatable sheath being rotatably disposed about at least a portion of the balloon and rotatable relative to the balloon, the rotatable sheath having a length less than that of the balloon, the rotatable sheath comprising a first end region, a second end region and a stent receiving region therebetween;
a stent, the stent having a proximal opening and a distal opening, the stent being expandable from a reduced stent state to an expanded stent state, in the reduced stent state the stent being disposed about the stent receiving region of the rotatable sheath, the first end of the rotatable sheath extending beyond a proximal end region of the stent and the second end region of the rotatable sheath extending beyond a distal end region of the stent, the stent at least partially constructed from a plurality of interconnected members, the interconnected members defining a plurality of cell openings, the cell openings positioned between the proximal opening and distal opening; and
a guidewire housing, the guidewire housing defining a guidewire lumen for passage of a guidewire therethrough, at least a portion of the guidewire housing being fixed attached to at least a proximal portion of the rotatable sheath, at least a portion of the guidewire housing extending distally through one of the cell openings.

2. The catheter assembly of claim 1 wherein at least a portion of the first end region of the rotatable sheath comprises a proximal flap, in the reduced stent state the proximal flap being positioned over a portion of the proximal end region of the stent, in the expanded stent state the proximal flap being withdrawn from about proximal end region of the stent.

3. The catheter assembly of claim 2 wherein the proximal flap has a first length in a region most proximate to the guidewire housing and a second length in a region furthest from the guidewire housing, the first length being less than the second length, the length of the proximal flap tapering therebetween.

4. The catheter assembly of claim 2 wherein the proximal flap defines a slot, the proximal flap having a circumferential length extending from a first side of the slot to the other side of the slot, the proximal flap having a longitudinal length, the longitudinal length being substantially the same throughout the circumferential length.

5. The catheter assembly of claim 1 wherein at least a portion of the second end region of the rotatable sheath comprises a distal flap, in the reduced stent state the distal flap being positioned over a portion of the distal end region of the stent, in the expanded stent state the distal flap being withdrawn from about distal end region of the stent.

6. The catheter assembly of claim 1 wherein at least a portion of the first end region of the rotatable sheath comprises a proximal flap, and at least a portion of the second end region of the rotatable sheath comprises a distal flap, in the reduced stent state the proximal flap being positioned over a portion of the proximal end region of the stent, in the expanded stent state the proximal flap being withdrawn from about proximal end region of the stent, in the reduced stent state the distal flap being positioned over a portion of the distal end region of the stent, in the expanded stent state the distal flap being withdrawn from about distal end region of the stent.

7. The catheter assembly of claim 6 wherein at least one of the proximal flap and the distal flap comprise a lubricious coating.

8. The catheter assembly of claim 1 wherein the rotatable sheath has an outer diameter, the outer diameter of the stent receiving region being less than the outer diameter of the first end region and the outer diameter of the a second end region.

9. The catheter assembly of claim 8 wherein the stent has an outer diameter, in the reduced stent state the outer diameter of the distal end region of the stent being no greater than the outer diameter of the second end region of the rotatable sheath.

10. The catheter assembly of claim 8 wherein the stent has an outer diameter, in the reduced stent state the outer diameter of the proximal end region of the stent being no greater than the outer diameter of the first end region of the rotatable sheath.

11. The catheter assembly of claim 1 wherein the guidewire housing is comprised of an outer guidewire housing and an inner guidewire housing, in the reduced stent state the outer guidewire housing being proximally adjacent to the proximal end region of the stent, at least a portion of the outer guidewire housing being radially offset from the proximal end region of the stent, the inner guidewire housing extending from the outer guide wire housing through at least a portion of the stent.

12. The catheter assembly of claim 1 wherein the guidewire housing compnses a proximal portion and a distal portion, the proximal portion having a diameter greater than that of the distal portion, in the reduced stent state the proximal portion of the guidewire housing being proximally adjacent to and radially offset from the proximal end region of the stent, the distal portion of the guidewire housing extending through at least a portion of the stent.

13. The catheter assembly of claim 1 wherein the rotatable sheath is expandable from a reduced sheath diameter when the balloon is in the reduced diameter configuration to an expanded sheath diameter when the balloon is in the expanded diameter configuration.

14. The catheter assembly of claim 13 wherein the balloon compnses a proximal balloon cone, a distal balloon cone and a rotatable sheath receiving region therebetween, the rotatable sheath being positioned on the rotatable sheath receiving region, such that the first portion of the rotatable sheath is distally adjacent the proximal balloon cone and the second portion of the rotatable sheath is proximally adjacent the distal balloon cone.

15. The catheter assembly of claim 14 wherein when the balloon is in the reduced diameter configuration, at least a portion of at least one of the proximal balloon cone and the distal balloon cone has an outer diameter greater than that of the rotatable sheath.

16. The catheter assembly of claim 14, wherein when the balloon is in the reduced diameter configuration, at least a portion of the distal balloon cone has an outer diameter greater than that of the distal end region of the stent.

17. The catheter assembly of claim 14, wherein when the balloon is in the reduced diameter configuration, at least a portion of the proximal balloon cone is radially offset from a portion of the proximal end region of the stent.

18. The catheter assembly of claim 1 further comprising a distal sleeve, the distal sleeve comprising a first sleeve region and a second sleeve region, in the reduced stent state at least a portion of the first sleeve region being disposed about the second end region of the rotatable sheath and the distal end region of the stent, the second sleeve region being rotatably engaged to a portion of the catheter shaft distally adjacent to the second end region of the rotatable sheath.

19. The catheter assembly of claim 18 wherein the first sleeve region is constructed of at least one first material and the second sleeve region is constructed of at least one second material, the at least on second material having a higher durometer value than the at least one first material.

20. The catheter assembly of claim 19 wherein in the expanded stent configuration the distal sleeve is retracted from about the second end region of the rotatable sheath and the distal end region of the stent.

21. The catheter assembly of claim 18 further comprising a proximal sleeve, the proximal sleeve comprising a first sleeve, region and a second sleeve region, in the reduced stent state at least a portion of the first sleeve region of the proximal sleeve being disposed about the first end region of the rotatable sheath and the proximal end region of the stent, the second sleeve region of the proximal sleeve being rotatably engaged to a portion of the catheter shaft proximally adjacent to the first end region of the rotatable sheath.

22. The catheter assembly of claim 21 wherein the proximal sleeve defines an opening the guidewire housing passing through the opening.

23. The catheter assembly of claim 22 wherein in the expanded stent configuration the proximal sleeve is retracted from about the first end region of the rotatable sheath and the proximal end region of the stent, the proximal sleeve being drawn proximally along the guidewire housing.

24. The catheter assembly of claim 1 wherein the stent is selected from at least one member of the group consisting of: a self-expanding stent, a balloon-expandable stent, a hybrid expandable stent and any combination thereof.

25. The catheter assembly of claim 24 wherein at least a portion of the stent is coated with at least one therapeutic agent.

26. The catheter assembly of claim 25 wherein the at least one therapeutic agent is at least one non-genetic therapeutic.

27. The catheter assembly of claim 25 wherein the at least one therapeutic agent is at least one genetic therapeutic agent.

28. The catheter assembly of claim 25 wherein the at least one therapeutic agent is at least one type of cellular material.

29. The catheter assembly of claim 25 wherein the at least one therapeutic agent comprises at least one polymer coating.

30. The catheter assembly of claim 1 further comprising a lubricious coating, the lubricious coating positioned between at least a portion of the rotatable sheath and the at least a portion of the catheter shaft.

31. The catheter assembly of claim 1 further comprising a rotatable collar, the rotatable collar rotatably disposed about a portion of the catheter shaft proximal of the rotatable sheath, at least a portion of the guidewire housing being engaged to at least a portion of the rotatable collar.

32. The catheter assembly of claim 1 wherein the rotatable sheath is at least partially constructed from a hydrophilic polymer material.

33. The catheter assembly of claim 1 wherein the rotatable sheath is at least partially constructed from a tecophilic material.

34. The catheter assembly of claim 1 wherein the rotatable sheath is at least partially constructed from a first material and a second material.

35. The catheter assembly of claim 34 wherein the rotatable sheath is at least partially constructed from at least one material of the group consisting of: hydrophilic polyurethanes, aromatic polyurethanes, polycarbonate base aliphatic polyurethanes, engineering polyurethane, elastomeric polyamides, block polyamide/ethers, polyether block amide, silicones, polyether-ester, polyester, polyester elastomer, polyethylene, polyamide, high-density polyethylene, polyetheretherketone, polyimide, polyetherimide, liquid crystal polymers, acetal, and any combination thereof.

36. The catheter assembly of claim 34 wherein the first material is a polymer matrix and the second material is at least one distinct member of reinforcing material at least partially supported within the polymer matrix.

37. The catheter assembly of claim 36 wherein polymer matrix is selected from at least one material from the group consisting of: hydrophilic polyurethanes, aromatic polyurethanes, polycarbonate base aliphatic polyurethanes, engineering polyurethane, elastomeric polyamides, block polyamide/ethers, polyether block amide, silicones, polyetherester, polyester, polyester elastomer, polyethylene and any combination thereof.

38. The assembly of claim 36 wherein the reinforcing material is selected from at least one material of the group consisting of polyamide, polyethylene, high-density polyethylene, polyetheretherketone, polyimide, polyetherimide, liquid crystal polymers, acetal, and any combination thereof.

39. A catheter assembly comprising:
  a catheter shaft having a proximal region and a distal region;
  a balloon disposed about a portion of the distal region of the catheter shaft, the balloon being expandable between a reduced diameter configuration and an expanded diameter configuration;
  a rotatable sheath, the rotatable sheath being rotatably disposed about at least a portion of the balloon and rotatable relative to the balloon, the rotatable sheath comprising a first end region, a second end region and a stent receiving region therebetween, the rotatable sheath having limited longitudinal movement relative to the balloon;
  a stent, the stent having a proximal opening and a distal opening, the stent being expandable from a reduced stent state to an expanded stent state, in the reduced stent state the stent being disposed about the stent receiving region of the rotatable sheath, the stent at least partially constructed from a plurality of interconnected members, the interconnected members defining a plurality of cell openings, the cell openings positioned between the proximal opening and distal opening;
  a guidewire housing, the guidewire housing defining a guidewire lumen for passage of a guidewire therethrough, at least a portion of the guidewire housing being fixed attached to at least an outer surface of the rotatable sheath; and
  further comprising a collar rotatably disposed about a portion of the catheter shaft, wherein the collar is directly attached to the guide wire housing to limit longitudinal movement of the rotatable sheath relative to the balloon.

40. The catheter assembly of claim 39 wherein the rotatable sheath is fixed longitudinally relative to the balloon.

* * * * *

UNITED STATES PATENT AND TRADEMARK OFFICE
CERTIFICATE OF CORRECTION

PATENT NO. : 7,686,841 B2  Page 1 of 1
APPLICATION NO. : 10/747546
DATED : March 30, 2010
INVENTOR(S) : Tracee Eidenschink It is certified that error appears in the above-identified patent and that said Letters Patent is hereby corrected as shown below:

Column 17
Line 25: delete "fied" and insert therefor -- filed --.

Column 19
Line 23: delete "compnses" and insert therefor -- comprises --.
Line 36: delete "compnses" and insert therefor -- comprises --.

Signed and Sealed this

Fourteenth Day of September, 2010

David J. Kappos
*Director of the United States Patent and Trademark Office*